US005871734A

United States Patent [19]
Lobb et al.

[11] Patent Number: 5,871,734
[45] Date of Patent: Feb. 16, 1999

[54] TREATMENT FOR ASTHMA WITH VLA-4 BLOCKING AGENTS

[75] Inventors: Roy R. Lobb, Westwood; Linda C. Burkly, West Newton, both of Mass.

[73] Assignee: Biogen, Inc., Cambridge, Mass.

[21] Appl. No.: 822,830

[22] Filed: Mar. 21, 1997

Related U.S. Application Data

[63] Continuation of Ser. No. 456,193, May 31, 1995, abandoned, which is a continuation-in-part of Ser. No. 374,331, Jan. 18, 1995, abandoned, which is a continuation-in-part of Ser. No. 256,631, Dec. 1, 1994, abandoned, which is a continuation-in-part of PCT/US93/00030 Jan. 12, 1993, which is a continuation-in-part of Ser. No. 821,768, Jan. 13, 1992, abandoned.

[51] Int. Cl.$^6$ ........................ A61K 39/395; A61K 35/12; A61K 38/17
[52] U.S. Cl. .................................... 424/144.1; 424/130.1; 424/133.1; 424/171.1; 424/143.1; 424/153.1; 424/154.1; 424/173.1; 514/2; 514/8; 514/885
[58] Field of Search .............................. 424/130.1, 133.1, 424/143.1, 154.1; 530/387.1, 388.22; 514/2, 8

[56] References Cited

U.S. PATENT DOCUMENTS

| 4,816,397 | 3/1989 | Boss et al. . |
| 4,833,092 | 5/1989 | Geysen . |
| 5,116,964 | 5/1992 | Capon . |
| 5,272,263 | 12/1993 | Heshon . |
| 5,730,978 | 3/1998 | Wayner et al. . |

FOREIGN PATENT DOCUMENTS

| 0 330 506 | 8/1989 | European Pat. Off. . |
| 387701 | 9/1990 | European Pat. Off. . |
| 9103252 | 3/1991 | WIPO . |
| WO 92/00751 | 1/1992 | WIPO . |
| WO 95.19790 | 1/1995 | WIPO . |

OTHER PUBLICATIONS

McNeil JNCI 87: 1658–1660 (1995).
Issekutz et al. J. Immunol. 147: 109–116 (1991).
Issekutz J. Immunol. 147: 4178–4184 (1991).
Mountain et al. Gen Eng Rev 110:1, 10–13 only (1992).
Edgington Biotechnology 10: 383–389 (1992).
Ward et al. Therapeutic Immunology 1: 165–171 (1994).
McCabe et al. Cell Immunol. 150: 364–375 (1993).
Paul Fundamental Immunol. 3$^{rd}$ Ed. 1993 Raven Press p. 242 only.
Osborn Cell 62: 3–6 1990.
Gundel et al. J Allergy Clin. Immunol. 85: 282 (1990).
Altman, L.K., (1991) "Despite Gains in Treatment, Asthma Worsens", *New York Times,* The Doctor's World, Mar. 26.
Weller, P.F., et al., (1991) "Human eosinophil adherence to vascular endothelium mediated by binding to vascular cell adhesion molecule 1 and endothelial leukocyte adhesion molecule 1", *Proceedings of the National Academy of Sciences,* vol. 88, pp. 7430–7433.

Walsh, G.M., et al., (1991) "Human Eosinophil, But Not Neutrophil, Adherence to IL–1–Stimulated Human Umbilical Vascular Endothelial Cells Is $\alpha_4\beta_1$ (Very Late Antigen–4) Dependent", *J. Immunol.,* vol. 146, pp. 3419–3423.
Bochner, B.S., et al., (1991) "Adhesion of Human Basophils, Eosinophils, and Neurophils to Interleukin 1–activated Human Vascular Endothelial Cells: Contributions of Endothelial Cell Adhesion Molecules", *J. Exp. Med.,* vol. 173, pp. 1553–1556.
Dobrina, A., et al., (1991) "Mechanisms of Eosinophil Adherence to Cultured Vascular Endohtelial Cells", *J. Clin. Invest.,* vol. 88, pp. 20–26.
Pulido, R., et al., (1991) "Functional Evidence for Three Distinct and Independently Inhibitable Adhesion Activated Mediated by the Human Integrin VLA–4", *J. Biol. Chem.,* vol. 266, No. 16, pp. 10241–10245.
Gundel, R.H., et al., (1991) "Endothelial Leukocyte Adhesion Molecule–1 Mediates Antigen–induced Acute Airway Inflammation and Late–phase Airway Obstruction in Monkeys", *J. Clin. Invest.,* vol. 88, pp. 1407–1411.
Parmentier, S., et al., (1991) "Role of Glycoprotein IIa (beta subuinit of very late activation antigens) in platelet functions", *Chemical Abstract,* vol. 115, No. 23, Abst. # 252 791h.
Onish, R., et al., (1991) "A monoclonal antibody, 2H7, which defines a new very late activation antigen, inhibits IL–2–mediated cell proliferation", *Chemical Abstract,* vol. 114, No. 9, Abst. #79 730s.
Sears, M.R., (1990) "Epidemiology of Asthma", in *Asthma as an Inflammatory Disease,* P. O'Byrne Ed., Marcel Dekker, Inc.; New York, pp. 15–48.
Cockcroft, D.W., (1990) "Atopy and Asthma", in *Asthma as an Inflammatory Disease,* P. O'Byrne Ed., Marcel Dekker, Inc.; New York, pp. 103–125.
Cuss, F.M.C., (1990) "The Pharmacology of Antiasthma Medications", in *Asthma as an Inflammatory Disease,* P. O'Byrne Ed., Marcel Dekker, Inc.; New York, pp. 199–250.
O'Byrne, P.M., (1990) "Airway Inflammation and Asthma", in *Asthma as an Inflammatory Disease,* P. O'Byrne Ed., Marcel Dekker, Inc.; New York, pp. 143–157.
Hogg, J.C., (1990) "Pathology of Asthma", in *Asthma as an Inflamatory Disease,* P. O'Byrne Ed., Marcel Dekker, Inc.; New York, pp. 1–13.
Chung, K.F., (1990) "Inflammatory Mediators in Asthma", in *Asthma as an Inflammatory Disease,* P. O'Byrne Ed., Marcel Dekker, Inc.; New York, pp. 159–183.

(List continued on next page.)

*Primary Examiner*—Lila Feisee
*Assistant Examiner*—Phillip Gambel
*Attorney, Agent, or Firm*—Louis Myers, Esq.; Lahive & Cockfield, LLP

[57] ABSTRACT

A method for the treatment of asthma is disclosed. The method comprises administration of an antibody, polypeptide or other molecule recognizing VLA-4, a protein expressed on the surface of certain leukocytes such as eosinophils.

22 Claims, 12 Drawing Sheets

OTHER PUBLICATIONS

Elices, M.J., et al., (1990) "VCAM-1 on Activated Endothelium Interacts with the Leukocyte Integrin VLA-4 at a Site Distinct from the VLA-4/Fibronectin Binding Site", *Cell,* vol. 60, pp. 577–584.

Devlin, J.J., et al., (1990) "Random Peptide Libraries: A Source of Specific Protein Binding Molecules", *Science,* vol. 249, pp. 40–46.

Scott, J.K., and Smith, G.P., (1990) "Searching for Peptide Ligands with an Epitope Library", *Science,* vol. 249, pp. 386–390.

Wegner, C.D., (1990) "Intercellular Adhesion Molecule-1 (ICAM-1) in the Pathogenesis of Asthma", *Science,* vol. 247, pp. 456–459.

Osborn, L., et al., (1989) "Direct cloning of vascular cell adhesion molecule 1, a cytokine–induced endothelial protein that binds to lymphocytes", *Cell,* vol. 59, pp. 1203–1211.

Abraham, W.M., (1989) "Pharmacology of Allergen–Induced Early and Late Airway Responses and Antigen–Induced Airway Hyperresponsiveness in Allergic Sheep", *Pulmonary Pharmacology,* vol. 2, pp. 33–40.

Ward, E.S., et al., (1989) "Binding Activities of a Repertoire of Single Immunoglobulin Variable Domains Secreted From *Escherichia coli*", *Nature,* vol. 341, pp. 544–546.

Abraham, W.M., et al., (1988) "Cellular Markers of Inflammation in the Airways of Allergic Sheep with or without Allergen–induced Late Responses", *Am. Rev. Respir. Dis.,* vol. 138, pp. 1565–1571.

Hemler, M.E., et al., (1987) "Characterization of the Cell Surface Heterodimer VLA–4 and Related Peptides", *J. Biol. Chem.,* vol. 262, No. 24, pp. 11478–11485.

Bluestein, H.G, et al., (1987) "Immunopathogenesis of the neuropsychiatric manifestations of systematic lupus erythematosus", *Chemical Abstracts,* vol. 106, No. 5, Abst. #31 234r.

Sanchez–Madrid, F., et al., (1986) "VLA–3: A novel polypeptide association whitin the VLA molecular complex: cell distribution and biochemical characterization", *Eur. J. Immunol.,* vol. 16, pp. 1343–1349.

Jones, P.T., et al., (1986) "Replacing the Complementarity-–Determining Regions in a Human Antibody with Those From a Mouse", *Nature,* vol. 321, pp. 522–525.

Kohler and Milstein, (1975) "Continuous Cultures of Fused Cells Secreting Antibody of Predefined Specificity", *Nature,* vol. 256, pp. 495–497.

Sherman–Gold, (1993) "Companies Pursue Therapies Based on Complex Cell Adhesion Molecules", *Genetic Engineering News,* Jul. 1993 issue, pp. 6–7, 14.

Harris, W.J., and Emery, S., (1993) "Therapeutic antibodies—the comming of age", *TIBTECH Forum,* vol. 11, Feb. 1993, pp. 42–44.

Jutila, M.A., et al., (1988) "Homing Receptors in Lymphocyte, Neutrophil, and Monocyte Interaction with Endothelial Cells", *First International Conference on Strusture, Function and Regulation Molecules Involved in Leukocyte Adhesion,* Sep. 28–Oct. 2, 1988.

Holzmann, B., and Weissman, I.L., (1989) "Integrin Molecules Involved in Lymphocyte Homing to Peyer's Patches", *Immunological Review,* No. 108, pp. 44–61.

Stoolman, L.M., (1989) "Adhesion Molecules Controlling Lymphocyte Migration", *Cell,* vol. 56, pp. 907–910.

Osband, M.E., and Ross, S., (1990) "Problems in the investigational study and clinical use of cancer immunotherapy", *Immunology Today,* vol. 11, No. 6, pp. 193–195.

Gundel, et al., (1991) "human Eosinophil Major Basic Protein Induces Airway Constriction and Airway Hyperresponsiveness in Primates", *J. Clin. Invest.,* vol. 87, pp. 1470–1473.

Hemler, et al., (1987) "The VLA Protein Family", *J. Biol. Chem.,* vol. 262, No. 7, pp. 3300–3309.

Lerner, E.A., (1981) "How to Make a Hybridoma", *Yale J. Biol. Med.,* vol. 54, pp. 387–402.

Starr, C., (1991) "Treating Asthma: A Killer Gathers Strength", *Drug Topics,* (cover story), issue of Apr. 8, pp. 38–48.

Lobb, R. et al., (1991) "Expression and Functional Characterization of a Soluble Form of Vascular Cell Adhesion Molecule I", *Biochem. Biophys. Res. Commun.,* vol. 178(3), pp. 1498–1504.

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 363 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..363

( i x ) FEATURE:
        ( A ) NAME/KEY: misc_feature
        ( B ) LOCATION: 1
        ( D ) OTHER INFORMATION: /note= "pBAG159 insert: HP1/2 heavy
            chain variable region"

( x i ) SEQUENCE DESCRIPTION: SEQ ID NO:1:

```
GAR GTC AAA CTG CAG CAG TCT GGG GCA GAG CTT GTG AAG CCA GGG GCC      48
Glu Val Lys Leu Gln Gln Ser Gly Ala Glu Leu Val Lys Pro Gly Ala
 1               5                  10                  15

TCA GTC AAG TTG TCC TGC ACA GCT TCT GGC TTC AAC ATT AAA GAC ACC      96
Ser Val Lys Leu Ser Cys Thr Ala Ser Gly Phe Asn Ile Lys Asp Thr
            20                  25                  30

TAT ATG CAC TGG GTG AAG CAG AGG CCT GAA CAG GGC CTG GAG TGG ATT     144
Tyr Met His Trp Val Lys Gln Arg Pro Glu Gln Gly Leu Glu Trp Ile
        35                  40                  45

GGA AGG ATT GAT CCT GCG AGT GGC GAT ACT AAA TAT GAC CCG AAG TTC     192
Gly Arg Ile Asp Pro Ala Ser Gly Asp Thr Lys Tyr Asp Pro Lys Phe
    50                  55                  60

CAG GTC AAG GCC ACT ATT ACA GCG GAC ACG TCC TCC AAC ACA GCC TGG     240
Gln Val Lys Ala Thr Ile Thr Ala Asp Thr Ser Ser Asn Thr Ala Trp
65                  70                  75                  80

CTG CAG CTC AGC AGC CTG ACA TCT GAG GAC ACT GCC GTC TAC TAC TGT     288
Leu Gln Leu Ser Ser Leu Thr Ser Glu Asp Thr Ala Val Tyr Tyr Cys
                85                  90                  95

GCA GAC GGA ATG TGG GTA TCA ACG GGA TAT GCT CTG GAC TTC TGG GGC     336
Ala Asp Gly Met Trp Val Ser Thr Gly Tyr Ala Leu Asp Phe Trp Gly
               100                 105                 110

CAA GGG ACC ACG GTC ACC GTC TCC TCA                                  363
Gln Gly Thr Thr Val Thr Val Ser Ser
               115                 120
```

( 2 ) INFORMATION FOR SEQ ID NO:2:

( i ) SEQUENCE CHARACTERISTICS:
        ( A ) LENGTH: 121 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Glu Val Lys Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys Asp Thr
            20                  25                  30
```

```
Tyr Met His Trp Val Lys Gln Arg Pro Glu Gln Gly Leu Glu Trp Ile
        35                      40                      45

Gly Arg Ile Asp Pro Ala Ser Gly Asp Thr Lys Tyr Asp Pro Lys Phe
        50                  55                  60

Gln Val Lys Ala Thr Ile Thr Ala Asp Thr Ser Ser Asn Thr Ala Trp
65                      70                      75                  80

Leu Gln Leu Ser Ser Leu Thr Ser Glu Asp Thr Ala Val Tyr Tyr Cys
                85                      90                      95

Ala Asp Gly Met Trp Val Ser Thr Gly Tyr Ala Leu Asp Phe Trp Gly
            100                     105                     110

Gln Gly Thr Thr Val Thr Val Ser Ser
            115                 120
```

( 2 ) INFORMATION FOR SEQ ID NO:3:

( i ) SEQUENCE CHARACTERISTICS:
        ( A ) LENGTH: 318 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..318
        ( D ) OTHER INFORMATION: /note= "HP1/2 light chain variable
            region"

( i x ) FEATURE:
        ( A ) NAME/KEY: misc_feature
        ( B ) LOCATION: 1
        ( D ) OTHER INFORMATION: /note= "pBAG172 insert: HP1/2 light
            chain variable region"

( x i ) SEQUENCE DESCRIPTION: SEQ ID NO:3:

```
AGT ATT GTG ATG ACC CAG ACT CCC AAA TTC CTG CTT GTT TCA GCA GGA      48
Ser Ile Val Met Thr Gln Thr Pro Lys Phe Leu Leu Val Ser Ala Gly
 1               5                   10                  15

GAC AGG GTT ACC ATA ACC TGC AAG GCC AGT CAG AGT GTG ACT AAT GAT      96
Asp Arg Val Thr Ile Thr Cys Lys Ala Ser Gln Ser Val Thr Asn Asp
            20                  25                  30

GTA GCT TGG TAC CAA CAG AAG CCA GGG CAG TCT CCT AAA CTG CTG ATA     144
Val Ala Trp Tyr Gln Gln Lys Pro Gly Gln Ser Pro Lys Leu Leu Ile
        35                  40                  45

TAT TAT GCA TCC AAT CGC TAC ACT GGA GTC CCT GAT CGC TTC ACT GGC     192
Tyr Tyr Ala Ser Asn Arg Tyr Thr Gly Val Pro Asp Arg Phe Thr Gly
        50                  55                  60

AGT GGA TAT GGG ACG GAT TTC ACT TTC ACC ATC AGC ACT GTG CAG GCT     240
Ser Gly Tyr Gly Thr Asp Phe Thr Phe Thr Ile Ser Thr Val Gln Ala
65                  70                  75                  80

GAA GAC CTG GCA GTT TAT TTC TGT CAG CAG GAT TAT AGC TCT CCG TAC     288
Glu Asp Leu Ala Val Tyr Phe Cys Gln Gln Asp Tyr Ser Ser Pro Tyr
                85                  90                  95

ACG TTC GGA GGG GGG ACC AAG CTG GAG ATC                             318
Thr Phe Gly Gly Gly Thr Lys Leu Glu Ile
                100                 105
```

( 2 ) INFORMATION FOR SEQ ID NO:4:

( i ) SEQUENCE CHARACTERISTICS:
        ( A ) LENGTH: 106 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Ser | Ile | Val | Met | Thr | Gln | Thr | Pro | Lys | Phe | Leu | Leu | Val | Ser | Ala | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Arg | Val | Thr | Ile | Thr | Cys | Lys | Ala | Ser | Gln | Ser | Val | Thr | Asn | Asp |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Val | Ala | Trp | Tyr | Gln | Gln | Lys | Pro | Gly | Gln | Ser | Pro | Lys | Leu | Leu | Ile |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Tyr | Tyr | Ala | Ser | Asn | Arg | Tyr | Thr | Gly | Val | Pro | Asp | Arg | Phe | Thr | Gly |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ser | Gly | Tyr | Gly | Thr | Asp | Phe | Thr | Phe | Thr | Ile | Ser | Thr | Val | Gln | Ala |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Glu | Asp | Leu | Ala | Val | Tyr | Phe | Cys | Gln | Gln | Asp | Tyr | Ser | Ser | Pro | Tyr |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Thr | Phe | Gly | Gly | Gly | Thr | Lys | Leu | Glu | Ile |
|-----|-----|-----|-----|-----|-----|-----|-----|-----|-----|
|     |     |     | 100 |     |     |     |     | 105 |     |

( 2 ) INFORMATION FOR SEQ ID NO: 5:

( i ) SEQUENCE CHARACTERISTICS:
        ( A ) LENGTH: 1347 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1338

( i x ) FEATURE:
        ( A ) NAME/KEY: VCAM-1 gene segment
        ( B ) LOCATION: 1..219
        ( D ) OTHER INFORMATION: This portion of the sequence
               corresponds, in part, to Exons I, II and III
               nucleotide sequence of Cybulsky et al. Proc. Nat'l.
               Acad. Sci. USA 88: 7861(1991).

( i x ) FEATURE:
        ( A ) NAME/KEY: Hinge region
        ( B ) LOCATION: 220..229
        ( D ) OTHER INFORMATION: This portion of the sequence
               corresponds, in part, to Fig. 12A in PCT/US92/02050 and
               represents the hinge region of Human IgG1 heavy chain
               constant region.

( i x ) FEATURE:
        ( A ) NAME/KEY: Heavy chain constant region 2
        ( B ) LOCATION: 230..338
        ( D ) OTHER INFORMATION: This portion of the sequence
               corresponds, in part, to Fig. 12A in PCT/US92/02050 and
               represents the heavy chain constant region 2 of Human
               IgG1 heavy chain constant region.

( i x ) FEATURE:
        ( A ) NAME/KEY: Heavy chain constant region 3
        ( B ) LOCATION: 339..446
        ( D ) OTHER INFORMATION: This portion of the sequence
               corresponds, in part, to Fig. 12A in PCT/US92/02050 and
               represents the heavy chain constant region 3 of Human
               IgG1 heavy chain constant region.

( x i ) SEQUENCE DESCRIPTION: SEQ ID NO: 5:

| ATG | CCT | GGG | AAG | ATG | GTC | GTG | ATC | CTT | GGA | GCC | TCA | AAT | ATA | CTT | TGG | 4 8 |
|-----|-----|-----|-----|-----|-----|-----|-----|-----|-----|-----|-----|-----|-----|-----|-----|-----|
| Met | Pro | Gly | Lys | Met | Val | Val | Ile | Leu | Gly | Ala | Ser | Asn | Ile | Leu | Trp |     |
| 110 |     |     |     | 115 |     |     |     |     | 120 |     |     |     |     | 125 |     |     |

| ATA | ATG | TTT | GCA | GCT | TCT | CAA | GCT | TTT | AAA | ATC | GAG | ACC | ACC | CCA | GAA | 9 6 |
|-----|-----|-----|-----|-----|-----|-----|-----|-----|-----|-----|-----|-----|-----|-----|-----|-----|
| Ile | Met | Phe | Ala | Ala | Ser | Gln | Ala | Phe | Lys | Ile | Glu | Thr | Thr | Pro | Glu |     |
|     |     |     |     | 130 |     |     |     |     | 135 |     |     |     |     | 140 |     |     |

| | | | | | | | | | | | | | | | | |
|---|---|---|---|---|---|---|---|---|---|---|---|---|---|---|---|---|
| TCT | AGA | TAT | CTT | GCT | CAG | ATT | GGT | GAC | TCC | GTC | TCA | TTG | ACT | TGC | AGC | 144 |
| Ser | Arg | Tyr | Leu | Ala | Gln | Ile | Gly | Asp | Ser | Val | Ser | Leu | Thr | Cys | Ser | |
| | | 145 | | | | | 150 | | | | | 155 | | | | |
| ACC | ACA | GGC | TGT | GAG | TCC | CCA | TTT | TTC | TCT | TGG | AGA | ACC | CAG | ATA | GAT | 192 |
| Thr | Thr | Gly | Cys | Glu | Ser | Pro | Phe | Phe | Ser | Trp | Arg | Thr | Gln | Ile | Asp | |
| | | 160 | | | | | 165 | | | | | 170 | | | | |
| AGT | CCA | CTG | AAT | GGG | AAG | GTG | ACG | AAT | GAG | GGG | ACC | ACA | TCT | ACG | CTG | 240 |
| Ser | Pro | Leu | Asn | Gly | Lys | Val | Thr | Asn | Glu | Gly | Thr | Thr | Ser | Thr | Leu | |
| | 175 | | | | | 180 | | | | | 185 | | | | | |
| ACA | ATG | AAT | CCT | GTT | AGT | TTT | GGG | AAC | GAA | CAC | TCT | TAC | CTG | TGC | ACA | 288 |
| Thr | Met | Asn | Pro | Val | Ser | Phe | Gly | Asn | Glu | His | Ser | Tyr | Leu | Cys | Thr | |
| 190 | | | | | 195 | | | | | 200 | | | | | 205 | |
| GCA | ACT | TGT | GAA | TCT | AGG | AAA | TTG | GAA | AAA | GGA | ATC | CAG | GTG | GAG | ATC | 336 |
| Ala | Thr | Cys | Glu | Ser | Arg | Lys | Leu | Glu | Lys | Gly | Ile | Gln | Val | Glu | Ile | |
| | | | | 210 | | | | | 215 | | | | | 220 | | |
| TAC | TCT | TTT | CCT | AAG | GAT | CCA | GAG | ATT | CAT | TTG | AGT | GGC | CCT | CTG | GAG | 384 |
| Tyr | Ser | Phe | Pro | Lys | Asp | Pro | Glu | Ile | His | Leu | Ser | Gly | Pro | Leu | Glu | |
| | | | 225 | | | | | 230 | | | | | 235 | | | |
| GCT | GGG | AAG | CCG | ATC | ACA | GTC | AAG | TGT | TCA | GTT | GCT | GAT | GTA | TAC | CCA | 432 |
| Ala | Gly | Lys | Pro | Ile | Thr | Val | Lys | Cys | Ser | Val | Ala | Asp | Val | Tyr | Pro | |
| | | 240 | | | | | 245 | | | | | 250 | | | | |
| TTT | GAC | AGG | CTG | GAG | ATA | GAC | TTA | CTG | AAA | GGA | GAT | CAT | CTC | ATG | AAG | 480 |
| Phe | Asp | Arg | Leu | Glu | Ile | Asp | Leu | Leu | Lys | Gly | Asp | His | Leu | Met | Lys | |
| | 255 | | | | | 260 | | | | | 265 | | | | | |
| AGT | CAG | GAA | TTT | CTG | GAG | GAT | GCA | GAC | AGG | AAG | TCC | CTG | GAA | ACC | AAG | 528 |
| Ser | Gln | Glu | Phe | Leu | Glu | Asp | Ala | Asp | Arg | Lys | Ser | Leu | Glu | Thr | Lys | |
| 270 | | | | | 275 | | | | | 280 | | | | | 285 | |
| AGT | TTG | GAA | GTA | ACC | TTT | ACT | CCT | GTC | ATT | GAG | GAT | ATT | GGA | AAA | GTT | 576 |
| Ser | Leu | Glu | Val | Thr | Phe | Thr | Pro | Val | Ile | Glu | Asp | Ile | Gly | Lys | Val | |
| | | | | 290 | | | | | 295 | | | | | 300 | | |
| CTT | GTT | TGC | CGA | GCT | AAA | TTA | CAC | ATT | GAT | GAA | ATG | GAT | TCT | GTG | CCC | 624 |
| Leu | Val | Cys | Arg | Ala | Lys | Leu | His | Ile | Asp | Glu | Met | Asp | Ser | Val | Pro | |
| | | | 305 | | | | | 310 | | | | | 315 | | | |
| ACA | GTA | AGG | CAG | GCT | GTA | AAA | GAA | TTG | CAA | GTC | GAC | AAA | ACT | CAC | ACA | 672 |
| Thr | Val | Arg | Gln | Ala | Val | Lys | Glu | Leu | Gln | Val | Asp | Lys | Thr | His | Thr | |
| | | 320 | | | | | 325 | | | | | 330 | | | | |
| TGC | CCA | CCG | TGC | CCA | GCA | CCT | GAA | CTC | CTG | GGG | GGA | CCG | TCA | GTC | TTC | 720 |
| Cys | Pro | Pro | Cys | Pro | Ala | Pro | Glu | Leu | Leu | Gly | Gly | Pro | Ser | Val | Phe | |
| | | 335 | | | | | 340 | | | | | 345 | | | | |
| CTC | TTC | CCC | CCA | AAA | CCC | AAG | GAC | ACC | CTC | ATG | ATC | TCC | CGG | ACC | CCT | 768 |
| Leu | Phe | Pro | Pro | Lys | Pro | Lys | Asp | Thr | Leu | Met | Ile | Ser | Arg | Thr | Pro | |
| 350 | | | | | 355 | | | | | 360 | | | | | 365 | |
| GAG | GTC | ACA | TGC | GTG | GTG | GTG | GAC | GTG | AGC | CAC | GAA | GAC | CCT | GAG | GTC | 816 |
| Glu | Val | Thr | Cys | Val | Val | Val | Asp | Val | Ser | His | Glu | Asp | Pro | Glu | Val | |
| | | | | 370 | | | | | 375 | | | | | 380 | | |
| AAG | TTC | AAC | TGG | TAC | GTG | GAC | GGC | GTG | GAG | GTG | CAT | AAT | GCC | AAG | ACA | 864 |
| Lys | Phe | Asn | Trp | Tyr | Val | Asp | Gly | Val | Glu | Val | His | Asn | Ala | Lys | Thr | |
| | | | 385 | | | | | 390 | | | | | 395 | | | |
| AAG | CCG | CGG | GAG | GAG | CAG | TAC | AAC | AGC | ACG | TAC | CGG | GTG | GTC | AGC | GTC | 912 |
| Lys | Pro | Arg | Glu | Glu | Gln | Tyr | Asn | Ser | Thr | Tyr | Arg | Val | Val | Ser | Val | |
| | | 400 | | | | | 405 | | | | | 410 | | | | |
| CTC | ACC | GTC | CTG | CAC | CAG | GAC | TGG | CTG | AAT | GGC | AAG | GAG | TAC | AAG | TGC | 960 |
| Leu | Thr | Val | Leu | His | Gln | Asp | Trp | Leu | Asn | Gly | Lys | Glu | Tyr | Lys | Cys | |
| | 415 | | | | | 420 | | | | | 425 | | | | | |
| AAG | GTC | TCC | AAC | AAA | GCC | CTC | CCA | GCC | CCC | ATC | GAG | AAA | ACC | ATC | TCC | 1008 |
| Lys | Val | Ser | Asn | Lys | Ala | Leu | Pro | Ala | Pro | Ile | Glu | Lys | Thr | Ile | Ser | |
| 430 | | | | | 435 | | | | | 440 | | | | | 445 | |
| AAA | GCC | AAA | GGG | CAG | CCC | CGA | GAA | CCA | CAG | GTG | TAC | ACC | CTG | CCC | CCA | 1056 |
| Lys | Ala | Lys | Gly | Gln | Pro | Arg | Glu | Pro | Gln | Val | Tyr | Thr | Leu | Pro | Pro | |
| | | | | 450 | | | | | 455 | | | | | 460 | | |

| | | | | | | | | | | | | | | | |
|---|---|---|---|---|---|---|---|---|---|---|---|---|---|---|---|
|TCC|CGG|GAT|GAG|CTG|ACC|AAG|AAC|CAG|GTC|AGC|CTG|ACC|TGC|CTG|GTC|
|Ser|Arg|Asp|Glu|Leu|Thr|Lys|Asn|Gln|Val|Ser|Leu|Thr|Cys|Leu|Val|
| |  |  |465|  |  |  |  |470|  |  |  |  |475|  |  |

1104

| | | | | | | | | | | | | | | | |
|---|---|---|---|---|---|---|---|---|---|---|---|---|---|---|---|
|AAA|GGC|TTC|TAT|CCC|AGC|GAC|ATC|GCC|GTG|GAG|TGG|GAG|AGC|AAT|GGG|
|Lys|Gly|Phe|Tyr|Pro|Ser|Asp|Ile|Ala|Val|Glu|Trp|Glu|Ser|Asn|Gly|
| | |480| | | | |485| | | | |490| | | |

1152

| | | | | | | | | | | | | | | | |
|---|---|---|---|---|---|---|---|---|---|---|---|---|---|---|---|
|CAG|CCG|GAG|AAC|AAC|TAC|AAG|ACC|ACG|CCT|CCC|GTG|CTG|GAC|TCC|GAC|
|Gln|Pro|Glu|Asn|Asn|Tyr|Lys|Thr|Thr|Pro|Pro|Val|Leu|Asp|Ser|Asp|
| |495| | | | |500| | | | |505| | | | |

1200

| | | | | | | | | | | | | | | | |
|---|---|---|---|---|---|---|---|---|---|---|---|---|---|---|---|
|GGC|TCC|TTC|TTC|CTC|TAC|AGC|AAG|CTC|ACC|GTG|GAC|AAG|AGC|AGG|TGG|
|Gly|Ser|Phe|Phe|Leu|Tyr|Ser|Lys|Leu|Thr|Val|Asp|Lys|Ser|Arg|Trp|
|510| | | | |515| | | | |520| | | | |525|

1248

| | | | | | | | | | | | | | | |
|---|---|---|---|---|---|---|---|---|---|---|---|---|---|---|
|CAG|CAG|GGG|AAC|GTC|TTC|TCA|TGC|TCC|GTG|ATG|CAT|GAG|GCT|CTG|CAC|
|Gln|Gln|Gly|Asn|Val|Phe|Ser|Cys|Ser|Val|Met|His|Glu|Ala|Leu|His|
| | | | |530| | | | |535| | | | |540| |

1296

| | | | | | | | | | | | | |
|---|---|---|---|---|---|---|---|---|---|---|---|---|
|AAC|CAC|TAC|ACG|CAG|AAG|AGC|CTC|TCC|CTG|TCT|CCG|GGT|AAA|
|Asn|His|Tyr|Thr|Gln|Lys|Ser|Leu|Ser|Leu|Ser|Pro|Gly|Lys|
| | | |545| | | | |550| | | | |555|

1338

TGAGTGCGG  1347

( 2 ) INFORMATION FOR SEQ ID NO: 6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 6..23
        ( D ) OTHER INFORMATION: This corresponds to Kinase
            Primer 370- 31.

( x i ) SEQUENCE DESCRIPTION: SEQ ID NO: 6:

| | | | | | | |
|---|---|---|---|---|---|---|
|TCGTC|GAC|AAA|ACT|CAC|ACA|TGC C|
| |Asp|Lys|Thr|His|Thr|Cys|
| |1| | | |5| |

24

( 2 ) INFORMATION FOR SEQ ID NO: 7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY:
        ( B ) LOCATION:
        ( D ) OTHER INFORMATION: This corresponds to Kinase
            Primer 370- 32.

( x i ) SEQUENCE DESCRIPTION: SEQ ID NO: 7:

GTAAATGAGT  GCGGCGGCCG  CCAA  24

( 2 ) INFORMATION FOR SEQ ID NO: 8:

( i ) SEQUENCE CHARACTERISTICS:
        ( A ) LENGTH: 115 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 8:

GCGGCCGCGG TCCAACCACC AATCTCAAAG CTTGGTACCC GGGAATTCAG ATCTGCAGCA    60

TGCTCGAGCT CTAGATATCG ATTCCATGGA TCCTCACATC CCAATCCGCG GCCGC    115

( 2 ) INFORMATION FOR SEQ ID NO: 9:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 21..41

( x i ) SEQUENCE DESCRIPTION: SEQ ID NO: 9:

GAGCTCGAGG CGGCCGCACC ATG CCT GGG AAG ATG GTC GTG    41
                                  Met Pro Gly Lys Met Val Val
                                  1                   5

( 2 ) INFORMATION FOR SEQ ID NO: 10:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 10:

AAGTCGACTT GCAATTCTTT TAC    23

( 2 ) INFORMATION FOR SEQ ID NO: 11:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 11:

TCGACGCGGC CGCG    14

( 2 ) INFORMATION FOR SEQ ID NO:12:

( i ) SEQUENCE CHARACTERISTICS:
        ( A ) LENGTH: 363 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..363

( i x ) FEATURE:
        ( A ) NAME/KEY: misc_feature
        ( B ) LOCATION: 1
        ( D ) OTHER INFORMATION: /note= "pBAG159 insert: HP1/2 heavy
            chain variable region"

( x i ) SEQUENCE DESCRIPTION: SEQ ID NO:12:

| CAR | GTC | AAA | CTG | CAG | CAG | TCT | GGG | GCA | GAG | CTT | GTG | AAG | CCA | GGG | GCC | 48 |
| Gln | Val | Lys | Leu | Gln | Gln | Ser | Gly | Ala | Glu | Leu | Val | Lys | Pro | Gly | Ala | |
| 1 | | | | 5 | | | | | 10 | | | | | 15 | | |

| TCA | GTC | AAG | TTG | TCC | TGC | ACA | GCT | TCT | GGC | TTC | AAC | ATT | AAA | GAC | ACC | 96 |
| Ser | Val | Lys | Leu | Ser | Cys | Thr | Ala | Ser | Gly | Phe | Asn | Ile | Lys | Asp | Thr | |
| | | | 20 | | | | | 25 | | | | | 30 | | | |

| TAT | ATG | CAC | TGG | GTG | AAG | CAG | AGG | CCT | GAA | CAG | GGC | CTG | GAG | TGG | ATT | 144 |
| Tyr | Met | His | Trp | Val | Lys | Gln | Arg | Pro | Glu | Gln | Gly | Leu | Glu | Trp | Ile | |
| | | 35 | | | | | 40 | | | | | 45 | | | | |

| GGA | AGG | ATT | GAT | CCT | GCG | AGT | GGC | GAT | ACT | AAA | TAT | GAC | CCG | AAG | TTC | 192 |
| Gly | Arg | Ile | Asp | Pro | Ala | Ser | Gly | Asp | Thr | Lys | Tyr | Asp | Pro | Lys | Phe | |
| | 50 | | | | | 55 | | | | | 60 | | | | | |

| CAG | GTC | AAG | GCC | ACT | ATT | ACA | GCG | GAC | ACG | TCC | TCC | AAC | ACA | GCC | TGG | 240 |
| Gln | Val | Lys | Ala | Thr | Ile | Thr | Ala | Asp | Thr | Ser | Ser | Asn | Thr | Ala | Trp | |
| 65 | | | | | 70 | | | | | 75 | | | | | 80 | |

| CTG | CAG | CTC | AGC | AGC | CTG | ACA | TCT | GAG | GAC | ACT | GCC | GTC | TAC | TAC | TGT | 288 |
| Leu | Gln | Leu | Ser | Ser | Leu | Thr | Ser | Glu | Asp | Thr | Ala | Val | Tyr | Tyr | Cys | |
| | | | | 85 | | | | | 90 | | | | | 95 | | |

| GCA | GAC | GGA | ATG | TGG | GTA | TCA | ACG | GGA | TAT | GCT | CTG | GAC | TTC | TGG | GGC | 336 |
| Ala | Asp | Gly | Met | Trp | Val | Ser | Thr | Gly | Tyr | Ala | Leu | Asp | Phe | Trp | Gly | |
| | | | 100 | | | | | 105 | | | | | 110 | | | |

| CAA | GGG | ACC | ACG | GTC | ACC | GTC | TCC | TCA | | | | | | | | 363 |
| Gln | Gly | Thr | Thr | Val | Thr | Val | Ser | Ser | | | | | | | | |
| | | 115 | | | | | 120 | | | | | | | | | |

( 2 ) INFORMATION FOR SEQ ID NO:13:

( i ) SEQUENCE CHARACTERISTICS:
        ( A ) LENGTH: 121 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| Gln | Val | Lys | Leu | Gln | Gln | Ser | Gly | Ala | Glu | Leu | Val | Lys | Pro | Gly | Ala |
| 1 | | | | 5 | | | | | 10 | | | | | 15 | |

| Ser | Val | Lys | Leu | Ser | Cys | Thr | Ala | Ser | Gly | Phe | Asn | Ile | Lys | Asp | Thr |
| | | | 20 | | | | | 25 | | | | | 30 | | |

| Tyr | Met | His | Trp | Val | Lys | Gln | Arg | Pro | Glu | Gln | Gly | Leu | Glu | Trp | Ile |
| | | 35 | | | | | 40 | | | | | 45 | | | |

| Gly | Arg | Ile | Asp | Pro | Ala | Ser | Gly | Asp | Thr | Lys | Tyr | Asp | Pro | Lys | Phe |
| | 50 | | | | | 55 | | | | | 60 | | | | |

| Gln | Val | Lys | Ala | Thr | Ile | Thr | Ala | Asp | Thr | Ser | Ser | Asn | Thr | Ala | Trp |
| 65 | | | | | 70 | | | | | 75 | | | | | 80 |

| Leu | Gln | Leu | Ser | Ser | Leu | Thr | Ser | Glu | Asp | Thr | Ala | Val | Tyr | Tyr | Cys |
| | | | | 85 | | | | | 90 | | | | | 95 | |

| Ala | Asp | Gly | Met | Trp | Val | Ser | Thr | Gly | Tyr | Ala | Leu | Asp | Phe | Trp | Gly |
| | | | 100 | | | | | 105 | | | | | 110 | | |

| Gln | Gly | Thr | Thr | Val | Thr | Val | Ser | Ser |
| | | 115 | | | | | 120 | |

TREATMENT FOR ASTHMA WITH VLA-4 BLOCKING AGENTS

This application is a file wrapper continuation of application Ser. No. 08/456,193 filed on May 31, 1995, now abandoned, which is a continuation-in-part of Lobb U.S. Ser. No. 08/374,331, now abandoned, filed Jan. 18, 1995, which is a continuation-in-part of Lobb U.S. Ser. No. 08/256,631, filed Jul. 12, 1994, now abandoned, and of PCT/US93/00030 filed Jan. 12, 1993, which is the continuation of part of Lobb 07/821,768, filed Jan. 13, 1992, now abandoned, all of which are hereby incorporated by reference.

FIELD OF THE INVENTION

The present invention relates to a treatment for asthma. More particularly, this invention relates to the use of antibodies recognizing Very Late Antigen-4 (VLA-4), a ligand on certain leukocytes for the endothelial cell receptor Vascular Cell Adhesion Molecule-1 (VCAM-1), in the treatment of asthma.

BACKGROUND OF THE INVENTION

Asthma is a condition of the respiratory tract characterized by widespread, reversible narrowing of the airways (bronchoconstriction) and increased sensitivity (hyperresponsiveness) of the airways to a variety of stimuli. The familiar symptomology of asthma, i.e., coughing, wheezing, chest tightness, dyspnea, is caused by airway smooth muscle contraction, increased bronchial mucus secretion, and inflammation. Though seldom fatal, asthma has been estimated to affect 10–20% of school-aged children around the world, and hospital admissions for asthma in children have increased dramatically in recent years, one survey for the United States indicating that hospital admissions for children under 15 with asthma increased by at least 145% between 1970 and 1984. (See, M. R. Sears, 1990 [1].) Overall, it is estimated that 10 million Americans (4% of the population) have asthma, and some S4 billion is spent in treatment per year. (L. K. Altman, 1991 [2]; C. Starr, 1991 [3].)

The causes of asthma are not completely understood, however the study of agents that trigger acute asthmatic episodes supports the theory that asthma is an immunological reaction by a subject in response to specific allergens of the subject's environment. These "triggers" exacerbate asthma by causing transient enhancement of airway hyperresponsiveness. Triggers that have been found to induce airway hyperresponsiveness include inhaled allergens, inhaled low molecular weight agents to which the subject has become sensitized (e.g., by occupational exposure), viral or mycoplasma respiratory infections, and oxidizing gases such as ozone and nitrogen dioxide. These "inducing" triggers can be distinguished from "inciting" triggers of bronchospastic episodes which include exercise, cold air, emotional stress, pharmacological triggers, inhaled irritants. The common feature of inducing triggers is that they are associated with airways inflammation; inciting triggers produce smooth muscle contractions (bronchospasms) which depend on the underlying degree of hyperresponsiveness, rather than increasing airways responsiveness themselves. (See, D. W. Cockcroft, 1990 [4].)

The recognition that airways inflammation is a cause of transient (acute) and also persistent airway hyperresponsiveness has had an impact on the treatment of asthma sufferers. Early treatments for asthma focused on bronchoconstriction and led to the development of many effective bronchodilator drugs. The most commonly prescribed were beta2-adrenoceptor agonists (epinephrine, isoproterenol, albuterol, salmeterol, etc.), xanthines (caffeine, theophylline, etc.) and cholinoceptor antagonists (atropine, acetylcholine, etc.). More recently, however, anti-inflammatory drugs have begun to replace bronchodilators as first-line treatments for asthma. Commonly prescribed anti-inflammatory agents for asthma include disodium cromoglycate (DSCG), nedocromil sodium, antihistamines such as ketotifen, and corticosteroids such as prednisolone. (See, F. M. C. Cuss, 1990 [5] and P. M. O'Byrne, 1990 [6].)

The inflammatory response in asthma is typical for tissues covered by a mucosa and is characterized by vasodilation, plasma exudation, recruitment of inflammatory cells such as neutrophils, monocytes, macrophages, lymphocytes and eosinophils to the sites of inflammation, and release of inflammatory mediators by resident tissue cells (e.g., mast cells) or by migrating inflammatory cells. (J. C. Hogg, 1990 [7].) In allergen-induced asthma, sufferers often exhibit a dual response to exposure to an allergen—an "early phase" response beginning immediately after exposure and lasting until 1–2 hours after exposure, followed by a "late phase" response beginning about 3 hours after exposure and lasting sometimes until 8–10 hours or longer after exposure. (D. W. Cockroft, 1990 [4].) Late phase response in allergen-induced asthma and persistent hyperresponsiveness have been associated with the recruitment of leukocytes, and particularly eosinophils, to inflamed lung tissue. (W. M. Abraham et al., 1988 [8].) Eosinophils are known to release several inflammatory mediators, e.g., 15-HETE, leukotriene $C_4$, PAF, cationic proteins, eosinophil peroxidase. (K. F. Chung, 1990 [9].)

Many of the drugs used to treat asthma have been found to block or neutralize the effects of the release of inflammatory mediators which regulate the inflammatory response. For example, beta2-adrenoceptor agonists and DSCG are potent stabilizers of mast cells, which are capable of releasing many mediators, including histamine, prostaglandins, leukotrienes, platelet activating factor (PAF), and chemotactic factors for neutrophils and eosinophils; corticosteroids, as another example, complex with steroid hormone receptors, which leads to the synthesis of proteins, such as lipocortins, that produce anti-inflammatory effects. (F. M. C. Cuss, 1990 [5].)

Although known asthma medications have some effect on leukocyte recruitment into the lung (W. M. Abraham et al., 1990 [8]), none of these drugs is effective to directly block migration of leukocytes into inflamed tissues.

Inflammatory leukocytes are recruited to sites of inflammation by cell adhesion molecules that are expressed on the surface of endothelial cells and which act as receptors for leukocyte surface proteins or protein complexes. Eosinophils have recently been found to participate in three distinct cell adhesion pathways to vascular endothelium, binding to cells expressing intercellular adhesion molecule-1 (ICAM-1), endothelial cell adhesion molecule-1 (ELAM-1), and vascular cell adhesion molecule-1 (YCAM-1). (P. F. Weller et al., 1991 [10]; G. M. Walsh et al., 1991 [11]; B. S. Bochner et al., 1991 [12]; and A. Dobrina et al., 1991 [13].) VCAM1 binds to the $\alpha_4\beta_1$, integrin, VLA-4, which is expressed on various lymphoid cells, including eosinophils (Weller et al., 1991 [10]; Elices et al. 1990 [14]). That eosinophils express VLA-4 differentiates them from other inflammatory cells such as neutrophils, which bind to ELAM-1 and ICAM-1 but not VCAM-1.

The VLA-4-mediated adhesion pathway was investigated in an asthma model to examine the possible role of VLA-4 in leukocyte recruitment to inflamed lung tissue. It has now been discovered that administering anti-VLA-4 antibody inhibits both the late phase response and airway hyperresponsiveness in allergic sheep. Surprisingly, administration of anti-VLA-4 led to a reduction in the number of both neutrophils and eosinophils in the lung at 4 hours after allergen challenge, even though both cells have alternate adhesion pathways by which they can be recruited to lung tissues. Also surprisingly, inhibition of hyperresponsiveness in the treated sheep was observed which continued to 1 week, even though infiltration of leukocytes, including neutrophils and eosinophils, was not significantly reduced over time.

SUMMARY OF THE INVENTION

The present invention provides novel methods for the treatment of asthma and further provides new pharmaceutical compositions useful in the treatment of asthma. In particular, the present invention provides a method comprising the step of administering to an asthma sufferer an effective amount of a VLA-4 blocking agent, e.g., an effective amount of an anti-VLA-4 antibody, such as monoclonal antibody HP1/2. The agent, e.g., an anti-VLA-4 antibody, is advantageously administered in vivo to a patient with chronic allergen-induced asthma, and serves to inhibit late phase response to allergens and to attenuate airway hyperresponsiveness.

DETAILED DESCRIPTION OF THE INVENTION

Figure 1:
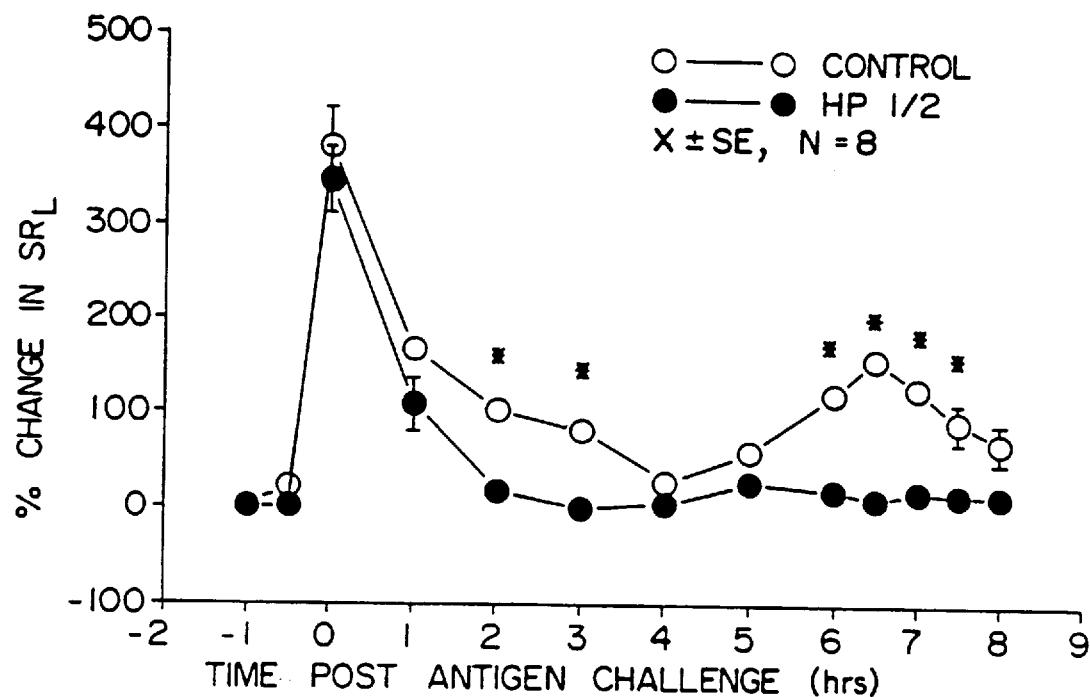
FIG. 1 is a graph depicting the effect of monoclonal antibody HP1/2 (intravenous) on the response to allergen (Ascaris suum antigen) in dual responder allergic sheep. Percentage change in specific lung resistance ($SR_L$) is measured over time post allergen challenge. Asterisks indicate statistically significant results.

The technology for producing monoclonal antibodies is well known. Briefly, an immortal cell line (typically myeloma cells) is fused to lymphocytes (typically splenocytes) from a mammal immunized with whole cells expressing a given antigen, e.g., VLA-4, and the culture supernatants of the resulting hybridoma cells are screened for antibodies against the antigen. (See, generally, Kohler et al., 1975 [15].)

Immunization may be accomplished using standard procedures. The unit dose and immunization regimen depend on the species of mammal immunized, its immune status, the body weight of the mammal, etc. Typically, the immunized mammals are bled and the serum from each blood sample is assayed for particular antibodies using appropriate screening assays. For example, anti-VLA-4 antibodies may be identified by immunoprecipitation of $^{125}$I-labeled cell lysates from VLA-4-expressing cells. (See, Sanchez-Madrid et al. 1986 [16] and Hemler et al. 1987 [17].) Anti-VLA-4 antibodies may also be identified by flow cytometry, e.g., by measuring fluorescent staining of Ramos cells incubated with an antibody believed to recognize VLA-4 (see, Elices et al., (1990) [14]). The lymphocytes used in the production of hybridoma cells typically are isolated from immunized mammals whose sera have already tested positive for the presence of anti-VLA-4 antibodies using such screening assays.

Typically, the immortal cell line (e.g., a myeloma cell line) is derived from the same mammalian species as the lymphocytes. Preferred immortal cell lines are mouse myeloma cell lines that are sensitive to culture medium containing hypoxanthine, aminopterin and thymidine ("HAT medium").

Typically, HAT-sensitive mouse myeloma cells are fused to mouse splenocytes using 1500 molecular weight polyethylene glycol ("PEG 1500"). Hybridoma cells resulting from the fusion are then selected using HAT medium, which kills unfused and unproductively fused myeloma cells (unfused splenocytes die after several days because they are not transformed). Hybridomas producing a desired antibody are detected by screening the hybridoma culture supernatants. For example, hybridomas prepared to produce anti-VLA-4 antibodies may be screened by testing the hybridoma culture supernatant for secreted antibodies having the ability to bind to a recombinant $\alpha_4$-subunit-expressing cell line, such as transfected K-562 cells (see, Elices et al. [14]).

To produce anti VLA-4-antibodies, hybridoma cells that tested positive in such screening assays were cultured in a nutrient medium under conditions and for a time sufficient to allow the hybridoma cells to secrete the monoclonal antibodies into the culture medium. Tissue culture techniques and culture media suitable for hybridoma cells are well known. The conditioned hybridoma culture supernatant may be collected and the anti-VLA-4 antibodies optionally further purified by well-known methods.

Alternatively, the desired antibody may be produced by injecting the hybridoma cells into the peritoneal cavity of an unimmunized mouse. The hybridoma cells proliferate in the peritoneal cavity, secreting the antibody which accumulates as ascites fluid. The antibody may be harvested by withdrawing the ascites fluid from the peritoneal cavity with a syringe.

Several anti-VLA-4 monoclonal antibodies have been previously described (see, e.g., Sanchez-Madrid et al., 1986 [16]; Hemler et al. (1987) [17]; Pulido et al. (1991) [19]). For the experiments herein, an anti-VLA-4 monoclonal antibody designated HP1/2 (obtained from Biogen, Inc., Cambridge, Mass.) was used. The variable regions of the heavy and light chains of the anti-VLA-4 antibody HP1/2 have been cloned, sequenced and expressed in combination with constant regions of human immunoglobulin heavy and light chains. Such a chimeric HP1/2 antibody is similar in specificity and potency to the murine HP1/2 antibody, and may be useful in methods of treatment according to the present invention. Similarly, humanized recombinant anti-VLA-4 antibodies may be useful in these methods. The HP1/2 $V_H$ DNA sequence and its translated amino acid sequences are set forth in SEQ ID NO: 1 SEQ ID NO: 12 and SEQ ID NO: 2 SEQ ID NO: 13, respectively. The HP1/2 $V_K$ DNA sequence and its translated amino acid sequence are set forth in SEQ ID NO: 3 and SEQ ID NO: 4, respectively.

Monoclonal antibodies such as HP1/2 and other anti-VLA-4 antibodies (e.g., Mab HP2/1, HP2/4, L25, P4C2) capable of recognizing the $\alpha$ chain of VLA-4 will be useful in the present invention. It is most preferred that the antibodies will recognize the B1 or B2 epitopes of the VLA-$\alpha_4$, chain (see, Pulido et al. (1991) [19]). While not wishing to be bound by one scientific theory, anti-VLA-4 antibodies used according to the method of the present invention may specifically inhibit, at least for an initial period following allergen challenge, the migration of VLA-4-expressing leukocytes to inflamed sections of the lung. This inhibition of VLA-4 leukocyte migration could, in turn, prevent secondary pathological effects of leukocyte infiltration, e.g., release of toxic substances, inducement of soluble inflammatory cell mediators, release or inducement of leukocyte chemotactic agents (such as neutrophil chemotactic factors), etc. As a result, late phase response to the allergen and continuing hypersensitivity of the airways may be attenuated. Alternatively, the anti-VLA-4 antibodies may attenuate signal transduction necessary for the release of inflammatory mediators and/or cell chemotactic agents.

The method of the present invention comprises administering to a mammal suffering from allergic asthma a composition comprising a VLA-4 blocking agent, e.g., an anti-VLA-4 antibody. The examples below set forth the results observed in asthmatic sheep. However, the similarity between physiological responses and pharmacological effects in sheep and in humans has been documented (see, e.g., W. M. Abraham, 1989 [20]); and similarities between sheep and other animal asthma models (rabbits, squirrel monkeys, guinea pigs, and sensitized dogs) have been noted (see, e.g., W. M. Abraham et al., 1988 [8]). Accordingly, the results reported herein will be relevant and applicable to, and the method claimed will be useful in, any mammal, including humans, suffering from allergic asthma.

The VLA-4 blocking agent, e.g., an anti-VLA-4 antibody, administered in accordance with the present invention may be administered prophylactically, before exposure to an asthma-inducing allergen. Beneficial effects will also be obtained if the agent, e.g., an antibody, is administered at the time of or immediately after allergen exposure, between early phase and late phase response to attenuate the severity of late phase response, or at any time following allergen exposure to reduce or eliminate airway hyperresponsiveness.

The VLA-4 blocking agent, e.g., an anti-VLA-4 antibody, can be administered in the form of a composition comprising an agent, e.g., an anti-VLA-4 antibody, and a pharmaceutically acceptable carrier. Preferably, the composition will be in a form suitable for intravenous injection. Also contemplated are compositions, e.g., antibody compositions, in the form of a sterile aqueous or phosphate-buffered saline solution which can be nebulized (atomized) and breathed directly into the lungs by the asthma sufferer, e.g., using an inhaler. Dosages will vary depending on the sensitivity of the asthma sufferer to particular allergens, the concentration of allergen on exposure and frequency/duration of exposure (s), the proposed mode of administration (e.g., injection or inhalation), the desired plasma level of an agent, e.g., an antibody, the effectiveness of a particular agent, e.g., a particular antibody or combination of antibodies, in suppressing airway responsiveness, the clearance rate or half-life of the composition, and other such factors familiar to physicians experienced in the treatment of allergic asthma. In general, in the case of an antibody, dosages will be calculated and adjusted to maintain a plasma level of antibody in the range from 1–1000 $\mu$g/ml, although higher or lower dosages may be indicated with consideration to the age, sensitivity, tolerance, and other characteristics of the patient, the acuteness of the flareup, the history and course of the disease, and other similar factors routinely considered by an attending physician. Depending on the potency and half-life of the antibody employed, it is preferred to use from about 0.05 mg/kg to 5.0 mg/kg of antibody, most preferably from 0.5 to 2.0 mg/kg of antibody, based on the weight of the patient receiving treatment.

Suitable pharmaceutical carriers include, e.g., sterile saline and physiological buffer solutions. Phosphate buffered saline (PBS) is preferred for inhalant administration. The pharmaceutical compositions may additionally be formulated to control the release of the active ingredients or to prolong their presence in the patient's system. Numerous suitable drug delivery systems are known for this purpose and include, e.g., hydrogels, hydroxmethylcellulose, microcapsules, liposomes, microemulsions, microspheres, and the like.

It will also be recognized that for the purposes of the present invention, antibodies capable of binding to the $\alpha_4$ subunit of VLA-4 should be employed. It is preferred that monoclonal antibodies be used.

In addition to naturally produced antibodies, suitable recombinant antibodies capable of binding to VLA-4 may alternatively be used. Such recombinant antibodies include antibodies produced via recombinant DNA techniques, e.g., by transforming a host cell with a suitable expression vector containing DNA encoding the light and heavy immunoglobulin chains of the desired antibody, and recombinant chimeric antibodies, wherein some or all of the hinge and constant regions of the heavy and/or the light chain of the anti-VLA-4 antibody have been substituted with corresponding regions of an immunoglobulin light or heavy chain of a different species (i.e., preferably the same species as the asthma sufferer being treated, to minimize immune response to the administered antibody). (See, e.g., P. T. Jones et al., 1986 [21], E. S. Ward et al., 1989 [22], and U.S. Pat. No. 4,816,397 (Boss et al.) [23], all incorporated herein by reference.)

Furthermore, VLA-4-binding fragments of anti-VLA-4 antibodies, such as Fab, Fab', F(ab')2, and F(v) fragments; heavy chain monomers or dimers; light chain monomers or dimers; and dimers consisting of one heavy chain and one light chain are also contemplated herein. Such antibody fragments may be produced by chemical methods, e.g., by cleaving an intact antibody with a protease, such as pepsin or papain, or via recombinant DNA techniques, e.g., by using host cells transformed with truncated heavy and/or light chain genes. Heavy and light chain monomers may similarly be produced by treating an intact antibody with a reducing agent such as dithiothreitol or β-mercaptoethanol or by using host cells transformed with DNA encoding either the desired heavy chain or light chain or both.

Also, from the discussion herein it will be apparent that other VLA-4 blocking agents can be used in the methods described herein. For the purposes of the invention a VLA-4 blocking agent refers to an agent, e.g., a polypeptide or other molecule, which can inhibit or block VLA-4-mediated binding or which can otherwise modulate VLA-4 function, e.g., by inhibiting or blocking VLA-4-ligand mediated VLA-4 signal transduction and which is effective in the treatment of asthma, preferably in the same manner as are anti-VLA-4 antibodies.

A VLA-4 blocking agent is a molecule which has one or more of the following properties: (1) it coats, or binds to, a VLA-4 antigen on the surface of a VLA-4 bearing cell with sufficient specificity to inhibit a VLA-4-ligand/VLA-4 interaction, e.g., the VLA-4/VCAM-1 interaction; (2) it coats, or binds to, a VLA-4 antigen on the surface of a VLA-4 bearing cell with sufficient specificity to modify, and preferably to inhibit, transduction of a VLA-4-mediated signal, e.g., VLA-4/VCAM-1-mediated signaling; (3) it coats, or binds to, a VLA-4-ligand, e.g., VCAM-1 or fibronectin, with sufficient specificity to inhibit the VLA-4/VLA-4-ligand interaction; (4) it coats, or binds to, a VLA-4-ligand, e.g., VCAM-1 or fibronectin, with sufficient specificity to modify, and preferably to inhibit, transduction of VLA-4-ligand mediated VLA-4 signaling, e.g., VCAM-1-mediated VLA-4 signaling. In preferred embodiments the VLA-4 blocking agent has one or both of properties 1 and 2. In other preferred embodiments the VLA-4 blocking agent has one or both of properties 3 and 4.

For purposes of the invention, any agent capable of binding to VLA-4 antigens on the surface of VLA-4 bearing cells and which effectively blocks or coats VLA-4 antigens, is considered to be an equivalent of the monoclonal antibody used in the examples herein.

As discussed herein, the blocking agents used in methods of the invention are not limited to antibodies or antibody derivatives, but may be other molecules, e.g., soluble forms of other proteins which bind VLA-4, e.g., the natural binding proteins for VLA-4. These binding agents include soluble VCAM-1 or VCAM-1 peptides, VCAM-1 fusion proteins, bifunctional VCAM-1/Ig fusion proteins, fibronectin, fibronectin having an alternatively spliced non-type III connecting segment, and fibronectin peptides containing the amino acid sequence EILDV or a similar conservatively substituted amino acid sequence. These binding agents can act by competing with the cell-surface binding protein for VLA4 or by otherwise altering VLA-4 function. For example, a soluble form of VCAM-1 (see, e.g., Osborn et al. 1989 [18]) or a fragment thereof may be administered to bind to VLA-4, and preferably compete for a VLA-4 binding site, thereby leading to effects similar to the administration of anti-VLA-4 antibodies. Soluble VCAM-1 fusion proteins can be used in the methods described herein. For example, VCAM-1, or a fragment thereof which is capable of binding to VLA-4 antigen on the surface of VLA-4 bearing cells, e.g., a fragment containing the two N-terminal domains of VCAM-1, can be fused to a second peptide, e.g., a peptide which increases the solubility or the in vivo life time of the VCAM-1 moiety. The second peptide can be a fragment of a soluble peptide, preferably a human peptide, more preferably a plasma protein, or a member of the immunoglobulin super family. In particularly preferred embodiments, the second peptide is IgG or a portion or fragment thereof, e.g., the human IgG1 heavy chain constant region. A particularly preferred fusion protein is the VCAM 2D-IgG fusion.

Included in the invention as VLA-4 blocking agents are (at least) peptides (preferably peptides of less than 5 or 10 amino acid resides in length), peptide mimetics, carbohydrates, and small molecules, such as oligosaccharides, capable of blocking VLA-4 in any of the ways described herein, e.g., by binding VLA-4 antigens on the surface of VLA-4-bearing cells or by binding to VLA-4-ligands. Small molecules such as oligosaccharides that mimic the binding domain of a VLA-4 ligand and fit the receptor domain of VLA-4 may also be employed. (See, J. J. Devlin et al., 1990 [24], J. K. Scott and G. P. Smith, 1990 [25], and U.S. Pat. No. 4,833,092 (Geysen) [26], all incorporated herein by reference.) Examples of small molecules useful in the invention can be found in Adams et al. U.S. Ser. No. 08/376,372, filed Jan. 23, 1995, hereby incorporated by reference.

In preferred embodiments more than one VLA-4 blocking agent is administered to a patient, e.g., a VLA-4 blocking agent which binds to VLA-4 can be combined with a VLA-4 blocking agent which binds to VCAM-1.

It is also contemplated that anti-VLA-4 antibodies may be used in combination with other antibodies having a therapeutic effect on airway responsiveness. For instance, to the extent that the beneficial effects reported herein are due to the inhibition of leukocyte recruitment to VCAM-1-expressing endothelium, combinations of anti-VLA-4 antibodies with other antibodies that interfere with the adhesion between leukocyte antigens and endothelial cell receptor molecules may be advantageous. For example, in addition to the use of anti-VLA-4 antibodies in accordance with this invention, the use of anti-ELAM-1, anti-VCAM-1 and/or anti-ICAM-1 antibodies may be advantageous. (See, Gundel et al. (1991) [27]; Wegner et al. (1990) [28].)

When formulated in the appropriate vehicle, the pharmaceutical compositions contemplated herein may be administered by any suitable means such as orally, intraesophageally or intranasally, intrabronchially (local treatment, e.g., via bronchoscope), as well as subcutaneously, intramuscularly, intravenously, intra-arterially, or parenterally. Ordinarily administration via inhalation is preferred.

In another aspect the invention features a chimeric molecule which includes: (1) a VLA-4 targeting moiety, e.g., a VCAM-1 moiety capable of binding to VLA-4 antigen on the surface of VLA-4 bearing cells; (2) optionally, a second peptide, e.g., one which increases solubility or in vivo life time of the VLA-4 targeting moiety, e.g., a member of the immunoglobulin super family or fragment or portion thereof, e.g., a portion or a fragment of IgG, e.g., the human IgG1 heavy chain constant region, e.g., $C_H2$ and $C_H3$ hinge regions; and (3) a toxin moiety. The VLA-4 targeting moiety can be any naturally occurring VLA-4 ligand or fragment thereof, e.g., a VCAM-1 peptide, fibronectin, fibronectin having an alternatively spliced non-type III connecting segment, and fibronectin peptides containing the amino acid sequence EILDV or a similar conservatively substituted amino acid sequence. A preferred targeting moiety is a soluble VCAM-1 fragment, e.g., the N-terminal domains 1 and 2 of the VCAM-1 molecule. The toxin moiety can be any agent which kills or inactivates a cell when the toxin is targeted to the cell by the VLA-4 targeting moiety. Toxin moieties include: cytotoxic peptide moieties, e.g., Diphtheria toxin A, Pseudomonas Exotoxin, Ricin A, Abrin A, Schigella toxin, or Gelonin; radionucleotides; and chemotherapeutic agents.

The chimeric molecule can be used to treat a subject, e.g., a human, at risk for a disorder, e.g., asthma, characterized by the presence of cells bearing VLA-4, and preferably activated VLA-4.

EXAMPLES

Experiments were performed essentially as described by Abraham et al. [8]. Briefly, allergic sheep having natural allergic cutaneous reaction to 1:1000 or 1:10,000 dilutions of *Ascaris suum* extract (Greer Diagnostics, Lenoir, N.C.) were tested, and sheep demonstrating both early and late phase airway response ("dual responders") to inhalation challenge with *Ascaris suum* antigen were selected. To measure breathing mechanics and physical changes in the airways, the sheep were restrained in a prone position with heads immobilized. A balloon catheter was advanced through one nostril under topical anesthesia with 2% lidocaine solution to the lower esophagus, and a cuffed endotracheal tube was advanced through the other nostril (using a flexible fiberoptic bronchoscope as a guide) for the measurement of airway mechanics and during aerosol challenges. Pleural pressure was estimated with the esophageal balloon catheter (filled with 1 ml of air) positioned 5–10 cm from the gastroesophageal junction. In this position, end expiratory pleural pressure ranged between −2 and −5 cm $H_2O$. Once the balloon was placed, it was secured so that it remained in position for the duration of the experiment. Lateral pressure in the trachea was measured with a sidehole catheter, (inner diam. 2.5 mm) advanced through and positioned distal to the tip of the endotracheal tube. Transpulmonary pressure (the difference between tracheal and pleural pressure) was measured with a differential pressure transducer catheter system (MP45, Validyne, Northridge, Calif.). The pressure transducer catheter system showed no phase shift between pressure and flow to a frequency of 9 $H_z$. Pulmonary resistance ($R_L$) was measured by connecting the proximal end of the endotracheal tube to a Fleich pneumotachograph (Dyna Sciences, Blue Bell, Pa.). Signals indicating flow and transpulmonary pressure were recorded on an oscilloscope recorder (Model DR-12; Electronics for Medicine, White Plains, N.Y.) linked to a computer for automatic calculation of pulmonary resistance ($R_L$) from transpulmonary pressure, respiratory volume (obtained by digital integration) and flow by the mid-volume technique, analyzed from 5–10 breaths. Thoracic gas volume ($V_{tg}$) was measured immediately after determination of $R_L$ in a constant volume body plethysmograph. Specific lung resistance ($SR_L$) was calculated from these values ($SR_L = V_{tg} \times R_L$).

Airway responsiveness was determined by performing dose response curves to inhaled carbachol. The dose response curves were plotted using measurements of $SR_L$ taken immediately after inhalation of buffer (PBS) alone and after each consecutive administration of 10 breaths of increasing concentrations of carbachol in PBS. The concentrations of carbachol were 0.25%, 0.5%, 1.0%, 2.0% and 4.0% wt/vol in PBS. The provocation test was discontinued when $SR_L$ increased over 400% from the post-PBS value or after the highest carbachol concentration had been administered. Airway responsiveness was determined by calculating from the dose response curves the cumulative carbachol dose in breath units (BU) that increased specific lung resistance 400% over the post buffer value ($PD_{400\%}$). one breath unit was defined as one breath of a 1% wt/vol carbachol solution. Thus, the greater the suppression of airway hyperresponsiveness, the greater the number of breath units would be required before observing the same bronchoconstriction as seen in the controls.

Each sheep was subjected to a trial as a control in which a placebo (PBS without additive) was used as a pretreatment 30 minutes before allergen challenge with *Ascaris suum* antigen (Greer Diagnostics, Lenoir, N.C.). Subsequently, the sheep were subjected to an identical trial, except that 1 mg/kg of monoclonal antibody HP1/2 was administered to each sheep 30 minutes prior to antigen challenge. The placebo (buffer control or isotope-matched antibody (1E6, anti-LFA3) control) and HP1/2 compositions were administered by intravenous injection. The HP1/2 composition (and the 1E6 control) was prepared by diluting pure antibody obtained from a hybridoma (Biogen, Inc., Cambridge Mass.) in sterile, endotoxin-free PBS and adjusting to deliver 1 mg/kg antibody based on the weight of each sheep. The antigen solution was delivered as an aerosol using a disposable medical nebulizer (RAINDROP®, Puritan Bennett, Lenexa, Kans.) that provided an aerosol with a mass median aerodynamic diameter of 3.2 μM (geometric SD 1.9) as determined by an Andersen cascade impactor. The *Ascaris suum* extract was diluted in PBS to a concentration of 82,000 Protein Nitrogen Units(PNU)/ml. The output of the nebulizer was directed into a plastic T-tube, one end of which was connected to the inspiratory port of a Harvard respirator. A dosimeter connected to the nebulizer consisting of a solenoid valve and a 20 psi compressed air source and the solenoid valve was activated at the beginning of the inspiratory cycle of the Harvard respirator for one second. The aerosol delivered at a tidal volume of 500 ml and a rate of 20 breaths per min. for 20 min. Each sheep was challenged with an equivalent dose of antigen (400 breaths) in the control and HP1/2 trials. Carbachol aerosols for the dose response curves were also generated by nebulizer as described above.

For cellular analysis, bronchoalveolar lavage (BAL) was performed on each sheep. The distal tip of the specially designed 80 cm fiberoptic bronchoscope was gently wedged into a randomly selected subsegmental bronchus. Lung lavage was performed by slow infusion and gentle aspiration of 3×30 ml of PBS (pH 7.4) at 39° C., using 30 ml syringes attached to the working channel of the bronchoscope. The lavage return was collected, strained through gauze to remove mucus and then centrifuged at 420 g for 15 min. Supernatant was decanted, and the cells were resuspended in PBS. An aliquot of the suspension was transferred to a hemocytometer chamber to estimate total cells. Total viable cells were estimated by trypan blue exclusion. A second aliquot of the cell suspension was spun in a cytospin (600 rpm for 10 minutes) and stained by Wright-Giemsa and observed at 100× to identify cell populations. 500 cells per slide were characterized to establish the differential cell counts. Cells characterized included epithelial cells, macrophages, basophils, monocytes and unidentifiable cells (grouped into a category termed "others"), in addition to lymphocytes, neutrophils and eosinophils.

Plasma level of antibody and white blood cell counts were determined from venous blood samples (approx. 5 ml) from peripheral leg vein or jugular vein.

Example 1

An airway challenge trial using eight dual responder allergic sheep was conducted according to the foregoing protocols. Baseline (BSL) airway responsiveness ($PD_{400\%}$) was established 2–3 days prior to antigen challenge and a baseline bronchoalveolar lavage (BAL) was performed one day prior to challenge. On challenge day, baseline values for specific lung resistance ($SR_L$) was measured, then the sheep were administered buffer (control) or HP1/2 by injection. After this first administration ("treatment"), $SR_L$ was measured, and 30 min. after treatment, the sheep were challenged with *Ascaris suum* antigen. $SR_L$ was measured immediately after challenge, hourly from 1–6 hours following challenge, every half-hour from 6.5 hours to 8 hours, and also at 24 hours, 48 hours and I week (i.e., 168 hours) after antigen challenge. BALs were performed following $SR_L$ measurements at 4, 8, 24 and 48 hours and at 1 week. For these studies, peripheral blood was drawn and total white blood cell counts and assessment of cell populations were taken before treatment (baseline), immediately after challenge, and at 1, 2, 3, 4, 6, 8, 24 and 48 hours, and 1 week after challenge. The results of this trial are shown in the figures:

FIG. 1 shows the effect of HP1/2 treatment on antigen-induced airway responses in the subject sheep. HP1/2 treatment resulted in significant (indeed, virtually complete) inhibition of the late phase response experienced by the controls.

Figure 2:
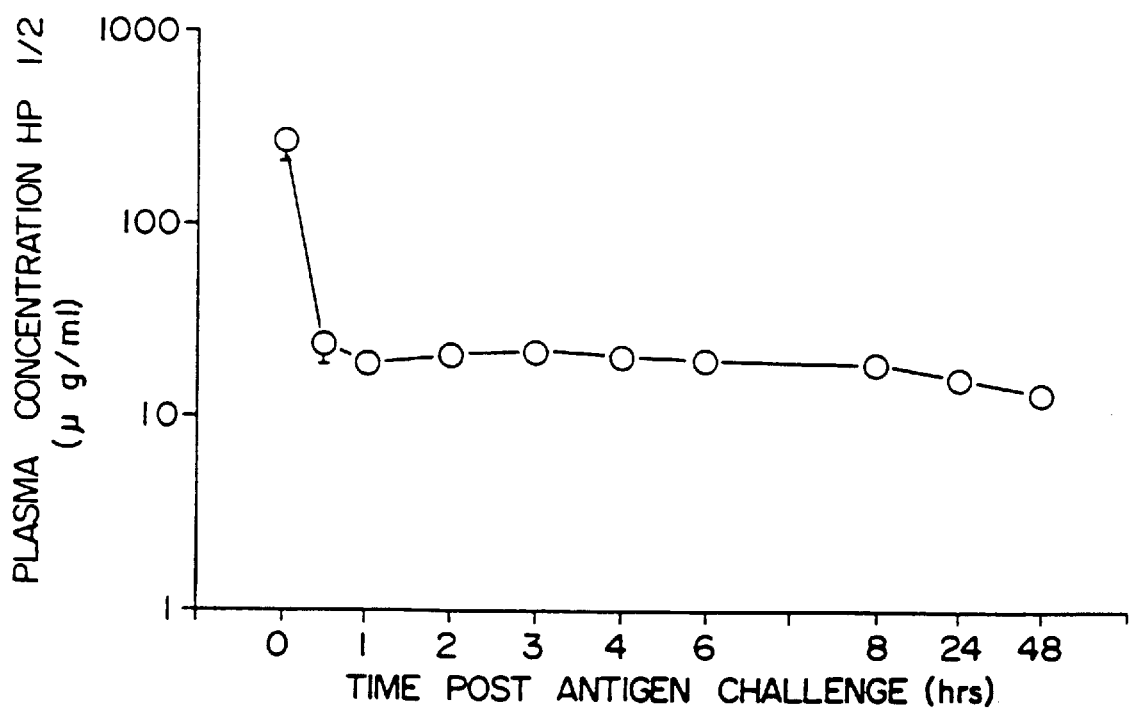
FIG. 2 is a graph depicting plasma concentration of monoclonal antibody HP1/2 (intravenous) in sheep, measured over time after initial administration.

FIG. 2 is a graph of plasma concentration of HP1/2 in µg/ml in the treated subjects, measured immediately following antigen challenge and then at 1, 2, 3, 4, 6, 8, 24 and 48 hours after challenge. After equilibration, the antibody concentration settled to a concentration of approximately 20 µg/ml, which concentration was maintained out to the 48-hour point.

Figure 3:
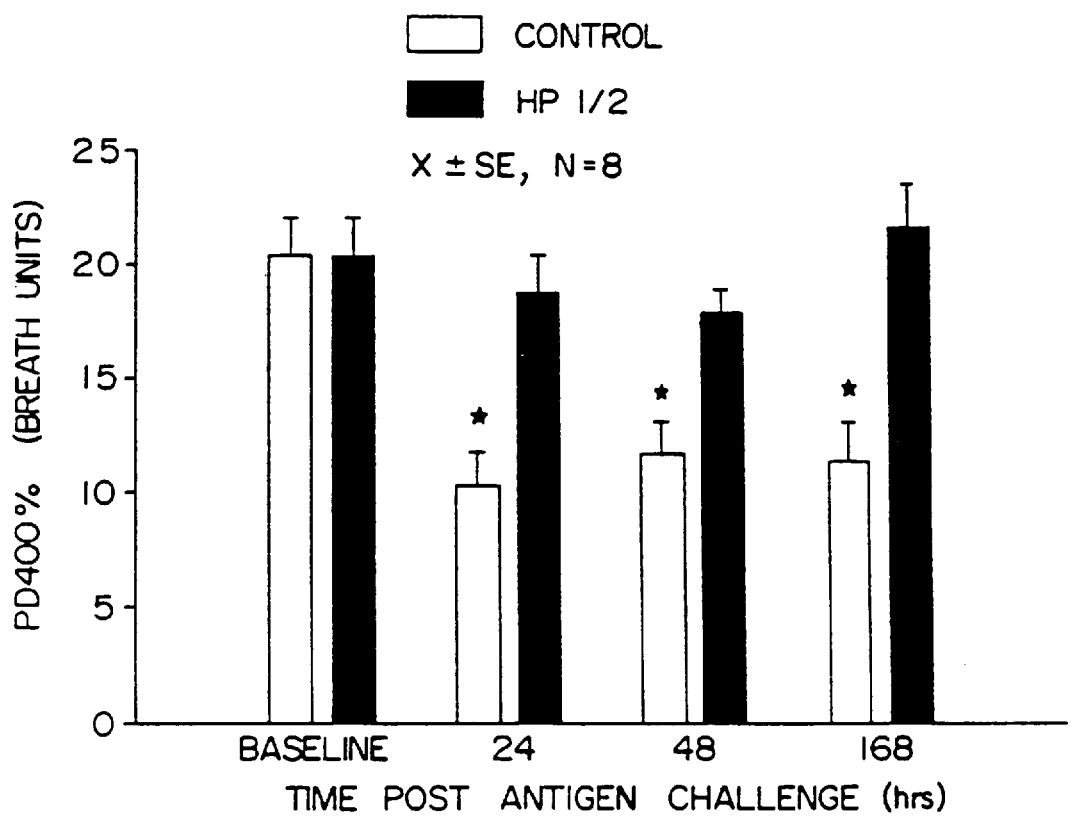
FIG. 3 is a graph depicting the effect of monoclonal antibody HP1/2 (intravenous) on airway hyperresponsiveness in dual responder sheep. Airway responsiveness, measured in breath units (BU) of cumulative breaths of a 1% weight/volume carbachol solution (a known bronchoconstrictor) that increases specific lung resistance 400% over the value obtained using diluent alone. Asterisks indicate statistically significant results.
Figure 4A:
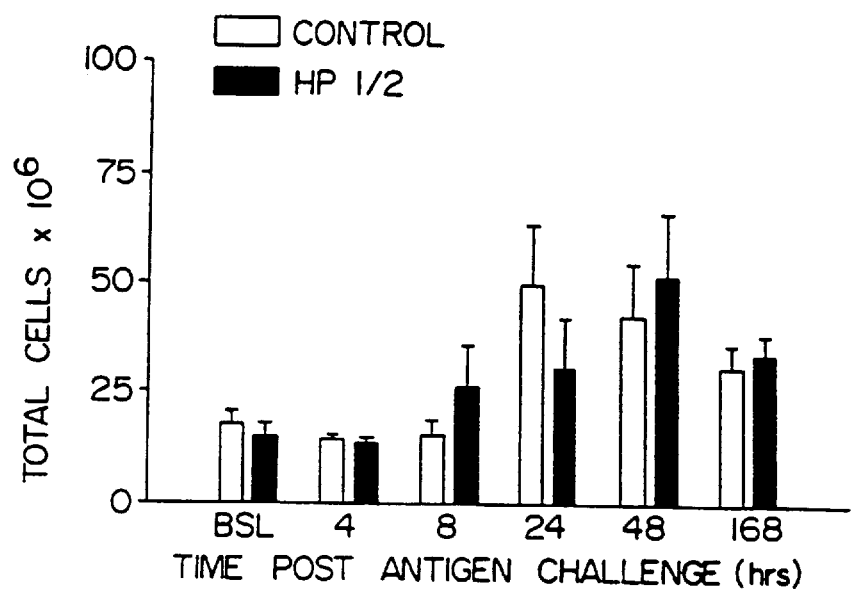
FIG. 4 is a series of four graphs showing the total cells and the levels of different leukocytes (lymphocytes, neutrophils, and eosinophils) detected by bronchoalveolar lavage in allergic sheep challenged with Ascaris suum antigen alone and after pretreatment with monoclonal antibody HP1/2 (intravenous). Total cells, and the percentage of total cells that were lymphocytes or neutrophils or eosinophils, were measured at 4-hour, 8-hour, 24-hour, 48-hour and 1-week time points post allergen challenge.
Figure 4B:
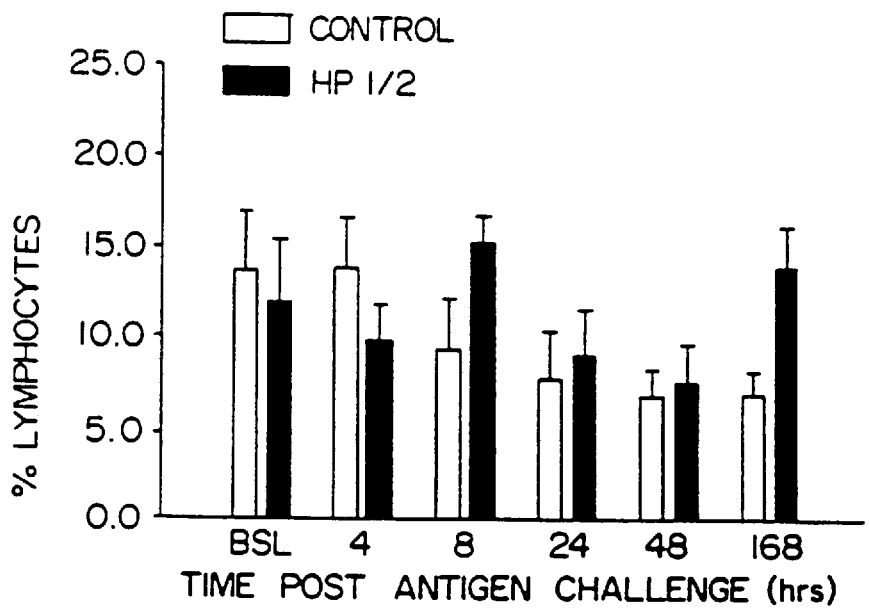
Figure 4C:
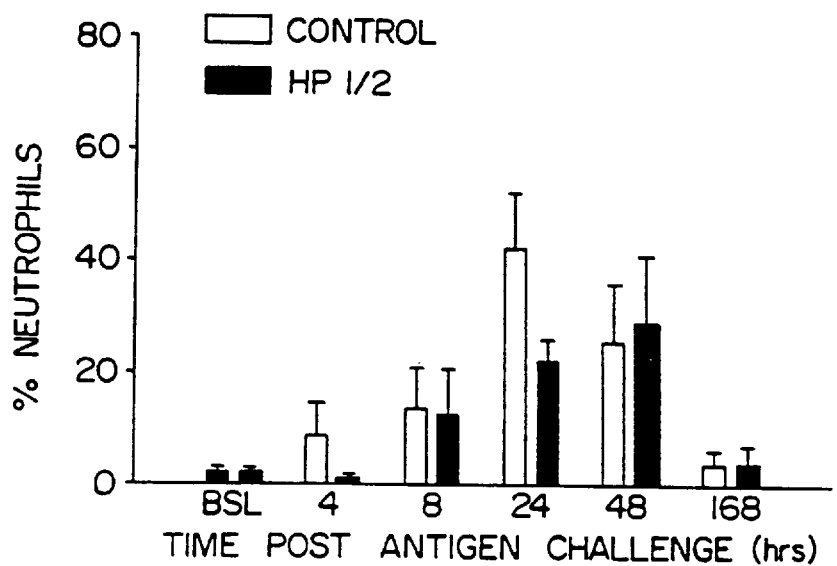
Figure 4D:
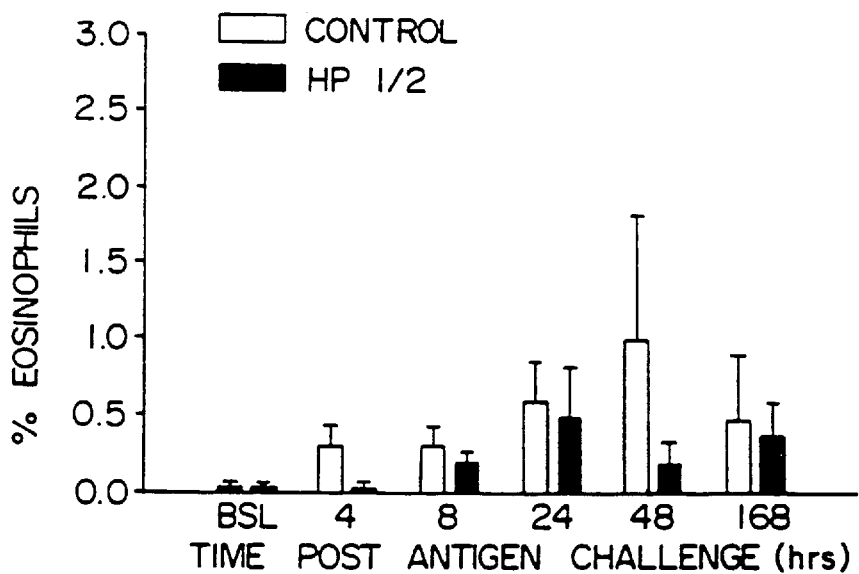

FIG. 3 is a graph showing the effect of HP1/2 treatment on airway responsiveness. At 24, 48, and 1 week after antigen challenge, treated subjects showed significant decrease in airway responsiveness. Even at 2 weeks after antigen challenge, treated subjects continued to show decreases in airway responsiveness. The fact that the virtually complete inhibitory effect of the antibody lasted out to 1 week is especially surprising and encouraging in terms of the therapeutic value of the treatment.

FIG. 4 is a series of graphs illustrating the results of BALs performed at 4, 8, 24 and 48 hours after antigen challenge, and at 1 week after antigen challenge. The results show no significant changes over controls in total cells recovered from treated subjects. However, treated subjects showed reduced levels of both neutrophils and eosinophils at the 4-hour time point after challenge. This is somewhat surprising, given that the administration of anti-VLA-4 would not be expected to influence neutrophil recruitment, since neutrophils do not express VLA-4. Also, both neutrophils and eosinophils express alternative ligands involved in adhesion to endothelium; both types of cells have been shown to bind to endothelial cells via the LFA-1/ICAM-1 pathway and the CDX/ELAM-1 pathway.

Similar therapeutic effects with the anti-VLA-4 antibody HP1/2 were observed when the subjects were treated with HP1/2 antibody 2 hours after antigen challenge as opposed to 30 minutes prior to challenge as described above. The effect of HP1/2 was dose-dependent. For example, reducing the dose to 0.2 mg/kg was not sufficient to protect against the late response. For the antigen challenge studies in which 1E6 (anti-LFA3) was used as an isotope-matched control antibody for the HP1/2 treatment, no effect on the early or late response was observed using 1E6 in a control trial. The 1E6-2C12 hybridoma cell line producing the 1E6 antibody has been deposited as ATCC HB 10693.

Example 2

A subsequent experiment was performed to investigate the efficacy of aerosol delivery of the antibody. The trials were performed essentially as described above, except that two sheep were used, and the HP1/2 was delivered via nebulizer in the form of an aerosol (dose=8 mg HP1/2 per animal, administered ½ hour prior to antigen challenge).

In control sheep (receiving placebo), the late phase response was characterized by an average increase in $SR_L$ of 126% of the baseline value, whereas when the sheep were treated with the anti-VLA-4 antibody, average rise in $SR_L$ was 26% of baseline. These results amount to approximately 80% inhibition of late phase response. The results also indicated about 70% inhibition of airway responsiveness at 24 hours. From this trial, it is apparent that inhalant delivery of the antibody may be used to obtain the benefits of this invention.

Figure 5:
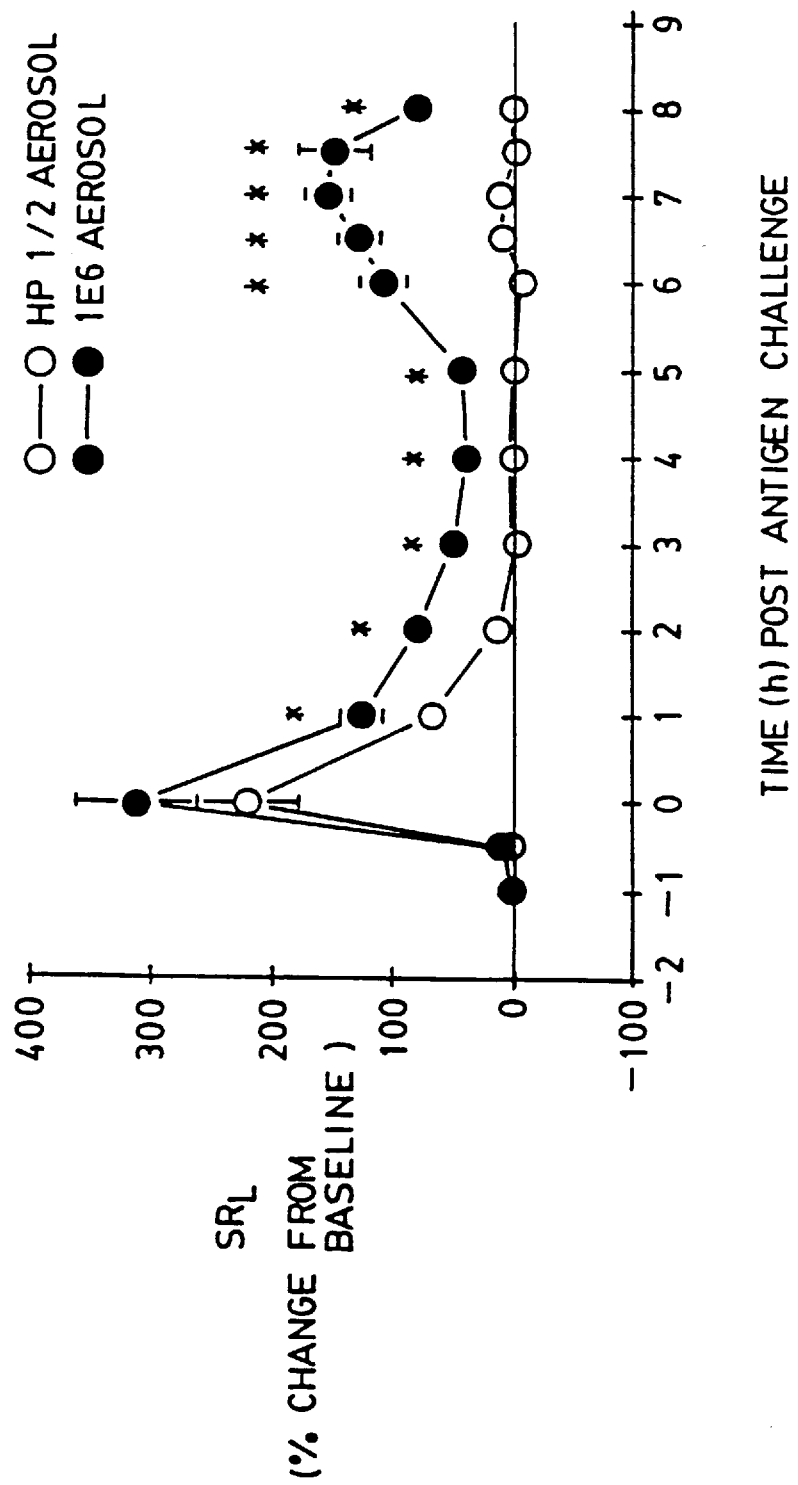
FIG. 5 is a graph depicting the effect of monoclonal antibody HPl/2 (16 mg, aerosol) and 1E6 (16 mg, aerosol) on the response to allergen (Ascaris suum antigen) in dual responder allergic sheep. Percentage change in specific lung resistance ($SR_L$) is measured over time post allergen challenge. Asterisks indicate statistically significant results.
Figure 6:
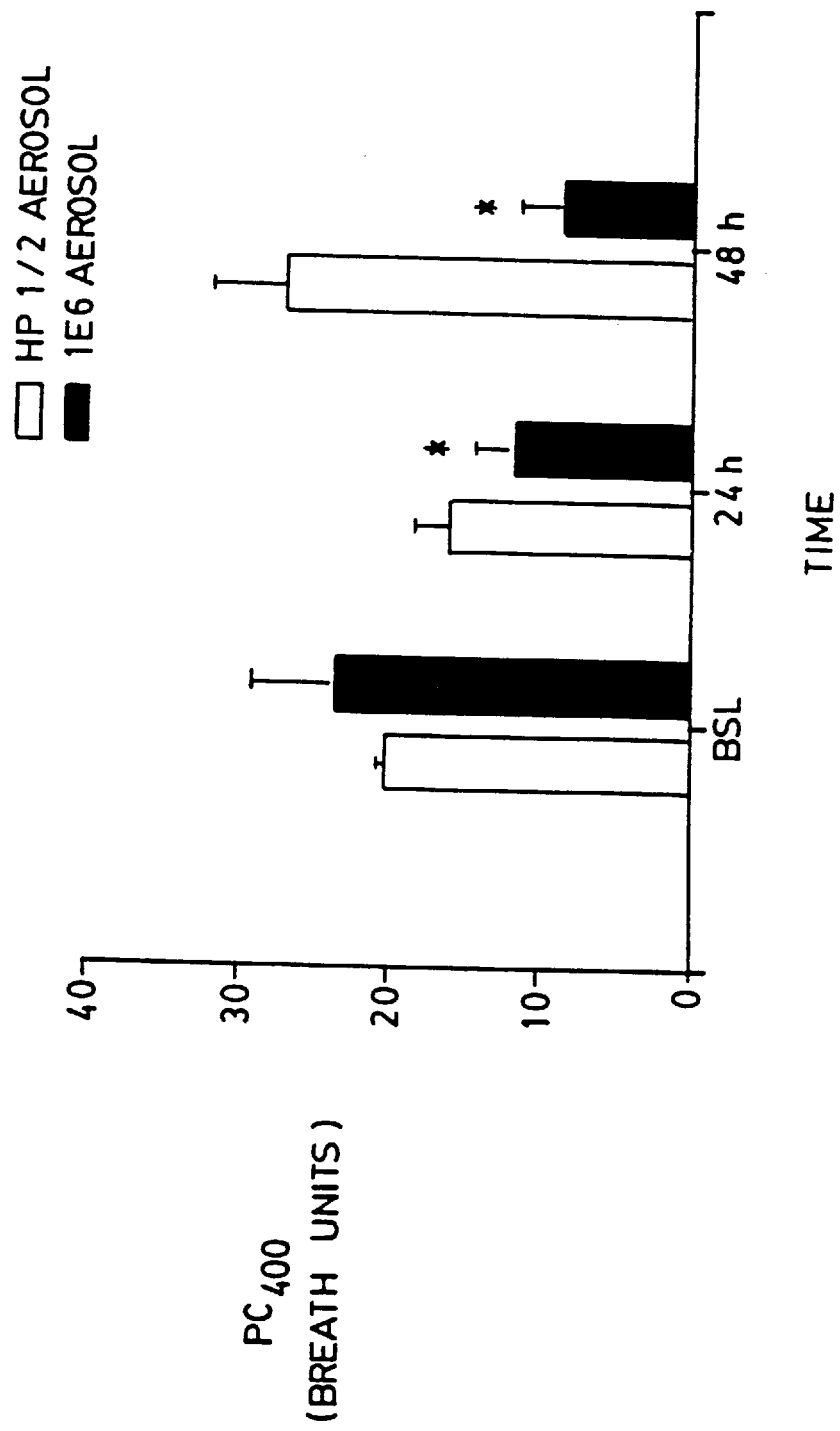
FIG. 6 is a graph depicting the effect of monoclonal antibody HP1/2 (16 mg, aerosol) and 1E6 (16 mg, aerosol) on airway hyperresponsiveness in dual responder sheep. Airway responsiveness, measured in breath units (BU) of cumulative breaths of a 1% weight/volume carbachol solution (a known bronchoconstrictor) that increases specific lung resistance 400% over the value obtained using diluent alone. Asterisks indicate statistically significant results.

These data were confirmed and extended to 5 sheep with controls (isotype-matched 1E6 (anti-LFA3) antibody control) using a 16 mg/kg aerosol dose of HP1/2 (n=5) or 1E6 (n=4). FIGS. 5 and 6 show that treatment with HP1/2 aerosol at this dose 30 minutes before antigen challenge is also effective in blocking the late response and airway hyperresponsiveness. HP1/2 aerosol treatment resulted in significant (indeed, virtually complete) inhibition of the late phase response experienced by the 1E6 controls. 1E6 aerosol treatment was without effect. Although comparable protection was achieved in both the intravenous and aerosol trials, the protection afforded by HP1/2 in the aerosol trials was achieved without detectable blood levels of the drug. This effect of HP1/2 is specific because the same dose of 1E6 had no protective effect (e.g., 1E6 treated animals showed a significant fall in $PC_{400}$, whereas HP1/2 blocked the effect). The differences in the physiological responses between HP1/2 and 1E6 are not the result of deficiencies in total WBC or differential counts between the groups. Total WBC and differential in both the HP1/2 and 1E6 groups showed a pattern of responses similar to those seen in the intravenous trials.

Example 3

Figure 7:
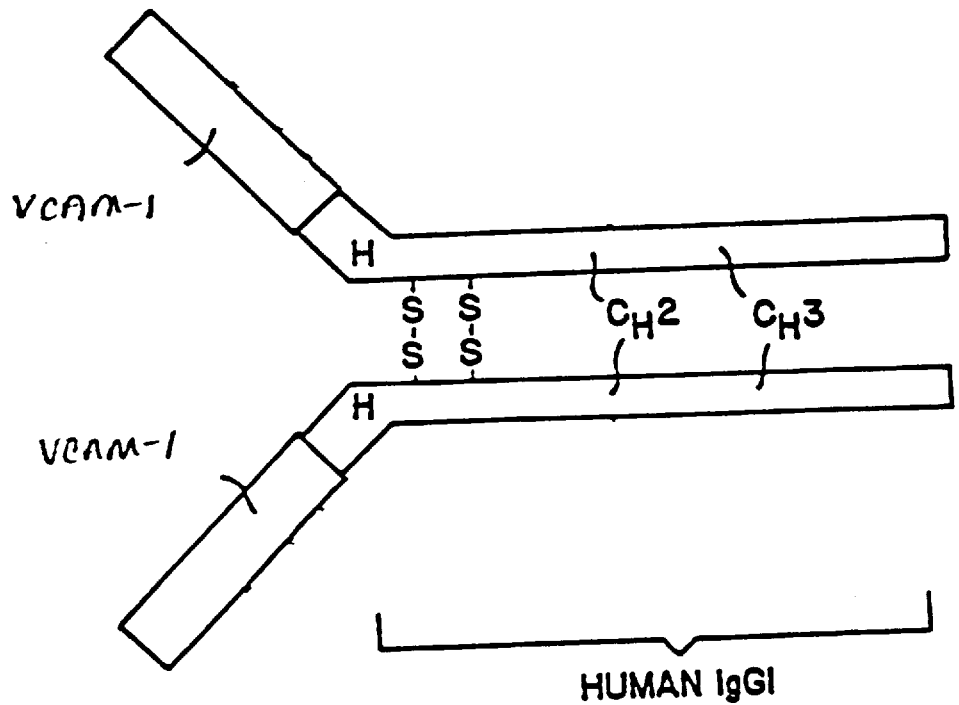
FIG. 7 is a schematic depicting structure of VCAM 2D-IgG fusion protein described in Example 3. VCAM 2D-IgG is a soluble form of the ligand for VLA4 (VCAM1) and consists of the two N-terminal domains of VCAM1 fused to the human IgG1 heavy chain constant region sequences (Hinges, $C_H2$ and $C_H3$).

The experiments described in Example 1 were repeated with a VCAM-Ig fusion protein (VCAM 2D-IgG) instead of an anti-VLA4 mAb. VCAM 2D-IgG is a soluble form of the ligand for VLA4 (VCAM1) which consists of the two N-terminal domains of VCAM 1 fused to the human IgG1 heavy chain constant region sequences (Hinges, $C_H2$ and $C_H3$). The VCAM 2D-IgG DNA sequence and its translated amino acid sequence are shown in SEQ ID NO: 5. FIG. 7 illustrates the fusion protein structure. The fusion protein was constructed by recombinant techniques as described below.

Isolation of cDNA of Human IgG1 Heavy Chain Region and Construction of Plasmid pSAB144

In order to isolate a cDNA copy of the human IgG1 heavy chain region, RNA was prepared from COS7 cells which has been transiently transfected by the plasmid VCAM1-IgG1 (also known as pSAB133). Construction of plasmid VCAM1-IgG1 is described in PCT patent application WO 90/13300. The RNA was reverse transcribed to generate cDNA using reverse transcriptase and random hexamers as the primers. After 30 min. at 42° C., the reverse transcriptase reaction was terminated by incubation of the reaction at 95° C. for 5 min. The cDNA was then amplified by PCR (Polymerase Chain Reaction, see, e.g., Sambrook et al., *Molecular Cloning*, Vol. 3, pp. 14.1–14.35 (Cold Spring Harbor; 1989) [29]) using the following kinased primers: 370-31 (SEQ ID NO: 6):

5'TCGTC GAC AAA ACT CAC ACA TGC C
       Asp Lys Thr His Thr Cys which contains a SalI site, and 370-32 (SEQ ID NO: 7):
5' GTAAATGAGT GCGGCGGCCG CCAA,
which encodes the carboxy terminal lysine of the IgG1 heavy chain constant region, followed by a NotI site.

The PCR amplified cDNA was purified by agarose gel electrophoresis and glass bead elution for cloning in plasmid pNN03. Plasmid pNN03 was constructed by removing the synthetic polylinker sequence from the commercially available plasmid pUC8 (Pharmacia, Piscataway, N.J.) by restriction endonuclease digestion and replacing the synthetic polylinker sequence with the following novel synthetic sequence (SEQ ID NO: 8):
GCGGCCGCGG TCCAACCACC AATCTCAAAG CTTGGTACCC GGGAATTCAG ATCTGCAGCA TGCTGAGCT CTAGATATCG ATTCCATGGA TCCT- CACATC CCAATCCGCG GCCGC.

The purified PCR amplified cDNA fragment was ligated to pNN03 which had been cleaved with EcoRV, dephosphorylated, and purified by low melt agarose gel electrophoresis. The ligation reaction was used to transform *E. coli* JA221 and the resulting colonies were screened for a plasmid containing an insert of approximately 700 bp. The identity of the correct insert was confirmed by DNA sequence analysis, and the plasmid was designated pSAB144.

Construction of Plasmid pSAB142

The plasmid pSAB142 was constructed as follows. cDNA prepared from COS cells transfected with pSAB133 (as described in the previous section) was subjected to PCR amplification using obligonucleotides 370-01 and 370-29. Oligonucleotide 370-01 includes a NotI site and the nucleotides corresponding to amino acids 1 through 7 of the VCAM-1 signal sequence (SEQ ID NO: 9):

5' GAGCTCGAGG CGGCCGCACC ATG CCT GGG AAG ATG GTC GTG
                                                     Met Pro Gly Lys Met Val Val

Oligonucleotide 370-29 corresponds to the VCAM-1 amino acids 214–219 and includes a SalI site (SEQ ID NO: 10):
5'AA GTC GAC TTG CAA TTC TTT TAC
The amplified DNA fragment was ligated to the vector fragment of pNN03, cleaved by EcoRV.

Construction of pSAB132 pJOD-S (Barsoum, J., *DNA and Cell Biol.*, 9, pp.293–300 (1990) [30]) was modified to insert a unique NotI site downstream from the adenovirus major late promoter so that NotI fragments could be inserted into the expression vector. pJOD-S was linearized by NotI cleavage of the plasmid DNA. The protruding 5' termini were blunt-ended using Mung Bean nuclease, and the linearized DNA fragment was purified by low melting temperature agarose gel electrophoresis. The DNA fragment was religated using T4 DNA ligase. The ligated molecules were then transformed into *E. coli* JA221. Colonies were screened for the absence of a NotI site. The resulting vector was designated pJOD-S delta NotI. pJOD-8 delta NotI was linearized using SalI and the 5' termini were dephosphorylated using calf alkaline phosphatase. The linearized DNA fragment was purified by low melting temperature agarose gel eletrophoresis and ligated in the presence of phosphorylated oligonucleotide ACE175, which has the following sequence (SEQ ID NO: 11):
TCGACGCGGC CGCG The ligation mixture was transformed into *E. coli* JA221, and colonies were screened for the presence of a plasmid having a NotI site. The desired plasmid was named pMDR901.

In order to delete the two SV40 enhancer repeats in the Sv40 promoter which controls transcription of the DHFR cDNA, pMDR901 and pJODαe-tPA (Barsoum, *DNA and Cell Biol.*, 9, pp. 293–300 (1990) [30]), both were cleaved with AatII and DraIII. The 2578 bp AatII-DraIII fragment from pMDR901 and the 5424 bp AatII-DraIII fragment from pJODαe-tPA were isolated by low melting temperature agarose gel electrophoresis and ligated together. Following transformation into *E. coli* JA221, the resulting plasmid, pMDR902, was isolated. pSAB132 was then formed by eliminating the EcoRI-NotI fragment of pMDR902 containing the adenovirus major late promoter and replacing it with an 839 bp EcoRI-NotI fragment from plasmid pCMV-B (Clontech, Palo Alto, Calif.) containing the human cytomegalovirus immediate early promoter and enhancer.

Construction of pSAB146 pSAB144 was cleaved with SalI and NotI, and the 693 bp fragment isolated. pSAB142 was cleaved with NotI and SalI and the 664 bp fragment was isolated. The two fragments were ligated to pSAB132 which had been cleaved with NotI, and the 5' termini dephosphorylated by calf alkaline phosphatase. The resulting plasmid, pSAB146, contained the DNA sequence encoding the VCAM-1 signal sequence, the amino terminal 219 amino acids of mature VCAM-1, ten amino acids of the hinge region of IgG1 and the CH2 and CH3 constant domains of IgG1.

Production of VCAM 2D-IgG from a stablytransformed CHO cell line

A recombinant VCAM 2D-IgG expression vector was constructed as described below and transfected into CHO cells to produce a cell line continuously secreting VCAM 2D-IgG.

The 1.357 kb NotI fragment containing the VCAM 2D-IgG coding sequence of pSAB146 was purified by agarose gel electrophoresis. This fragment was ligated into the NotI cloning site of the expression vector pMDR901, which uses the adenovirus 2 major late promoter for heterologous gene expression and the selectable, amplifiable dihydrofolate reductase (dhfr) marker. The ligated DNA was used to transform E. coli DH5. Colonies containing the plasmid with the desired, correctly oriented insert were identified by the presence of 5853 and 3734 bp fragments upon digestion with Hind III; and 4301, 2555, 2293, and 438 bp fragments upon digestion with BglII. The resultant recombinant VCAM 2D-IgG expression vector was designated pEAG100. The identity of the correct insert was confirmed by DNA sequence analysis.

The recombinant expression plasmid pEAG 100 was electroporated into dhfr-deficient CHO cells according to the published protocol of J. Barsoum (DNA Cell Biol 9: 293–300, 1990 [30]), with the following changes: 200 μg of PvuI-linearized pEAG100 plasmid and 200 μg of sonicated salmon sperm DNA were used in the electroporation protocol. In addition, cells were selected in alpha-complete medium supplemented with 200 nM methotrexate.

To determine expression levels of secreted VCAM 2D-IgG, clones were transferred to a flat bottom 96 well microtiter plate, grown to confluency and assayed by ELISA as described below.

Wells of Immulon 2 plates (Dynatech, Chantilly, Va.) were each coated with anti-VCAM MAb 4B9 (isolated and purified on Protein A Sepharose as described by Carlos et al, 1990 [56]) with 100 μl of anti-VCAM 4B9 MAb diluted to 10 μg/ml in 0.05M sodium carbonate/bicarbonate buffer, pH 9.6, covered with Parafilm, and incubated overnight at 4° C. The next day, the plate contents were dumped out and blocked with 200 μl/well of a block buffer (5% fetal calf serum in 1× PBS), which had been filtered through a 2 filter. The buffer was removed after a 1 hour incubation at room temperature and the plates were washed twice with a solution of 0.05% Tween-20 in 1× PBS. Conditioned medium was added at various dilutions. As a positive control, an anti-mouse Ig was also included. Block buffer and LFA-3TIP constituted as negative controls. The samples and controls were incubated at room temperature for 2 hours.

The plates were then washed twice with a solution of 0.05% Tween-20 in 1× PBS. Each well, except for the positive control well, was then filled with 50 μl of a 1:2000 dilution of HRP-Donkey anti-human IgG (H+L) (Jackson Immune Research Laboratories, Inc.; West Grove, Pa.) in block buffer. The positive control well was filled with 50 μl of a 1:2000 dilution of HRP-Goat anti-mouse IgG (H+L) (Jackson Immune Research Laboratories, Inc.; West Grove, Pa.) in block buffer. The plates were then incubated for 1 hour at room temperature.

The HRP conjugated Ab solutions were removed, and the wells were washed twice with 0.05% Tween-20 in 1× PBS. Then, 100 μl of HRP-substrate buffer was added to each well at room temperature. HRP-substrate buffer was prepared as follows: 0.5 ml of 42 mM 3,3', 5,5'-tetramethylbenzidine (TMB), (ICN Immunobiologicals, Lisle, S.C., Catalogue No. 980501) in DMSO (Aldrich) was slowly added to 50 ml of substrate buffer (0.1M sodium acetate/citric acid, pH 4.9); followed by addition of 7.5 μl of 30% hydrogen peroxide (Sigma, Catalogue No. H-1009).

The development of a blue color in each well was monitored at 650 nm on a microtiter plate reader. After 7–10 minutes, the development was stopped by the addition of 100 μl of 2N Sulfuric acid. The resulting yellow color was read at 450 nm on a microtiter plate reader. A negative control well was used to blank the machine.

Purification of VCAM 2D-IgG

CHO cells expressing VCAM 2D-IgG were grown in roller bottles on collagen beads. Conditioned medium (5 Liters) was concentrated to 500 ml using an Amicon S1Y10 spiral ultrafiltration cartridge (Amicon, Danvers, Mass.). The concentrate was diluted with 1 liter of Pierce Protein A binding buffer (Pierce, Rockford, Ill.) and gravity loaded onto a 10 ml Protein A column (Sepharose 4 Fast Flow, Pharmacia, Piscataway, N.J.). The column was washed 9 times with 10 ml of Protein A binding buffer and then 7 times with 10 ml of PBS. VCAM 2D-IgG was eluted with twelve-5 ml steps containing 25 mM $H_3PO_4$ pH 2.8, 100 mM NaCl. The eluted samples were neutralized by adding 0.5M $Na_2HPO_4$ pH 8.6 to 25 mM. Fractions were analyzed for absorbance at 280 nm and by SDS-PAGE. The three peaks fractions of highest purity were pooled, filtered, aliquoted and stored at −70° C. By SDS-PAGE, the product was greater than 95% pure. The material contained less than 1 endotoxin unit per mg of protein. In some instances, it was necessary to further purify the Protein A eluate product on Q-Sepharose FF (Pharmacia). The protein A eluate was diluted with 3 volumes of 25 mM Tris HCl pH 8.0 and loaded onto a Q-Sepharose FF column at 10 mg VCAM 2D-IgG per ml of resin. The VCAM 2D-IgG was then eluted from the Q- Sepharose with PBS.

Evaluation of VCAM 2D-IgG

An airway challenge trial using five pairs of responder allergic sheep was conducted according to the foregoing protocols in order to investigate the efficacy of VCAM1-IgG1 (VCAM-Ig) fusion protein in the sheep model of airways hyper-responsiveness. The efficacy of the aerosol delivery of the VCAM-Ig was investigated. VCAM-Ig was delivered via nebulizer in the form of an aerosol.

Figure 8:
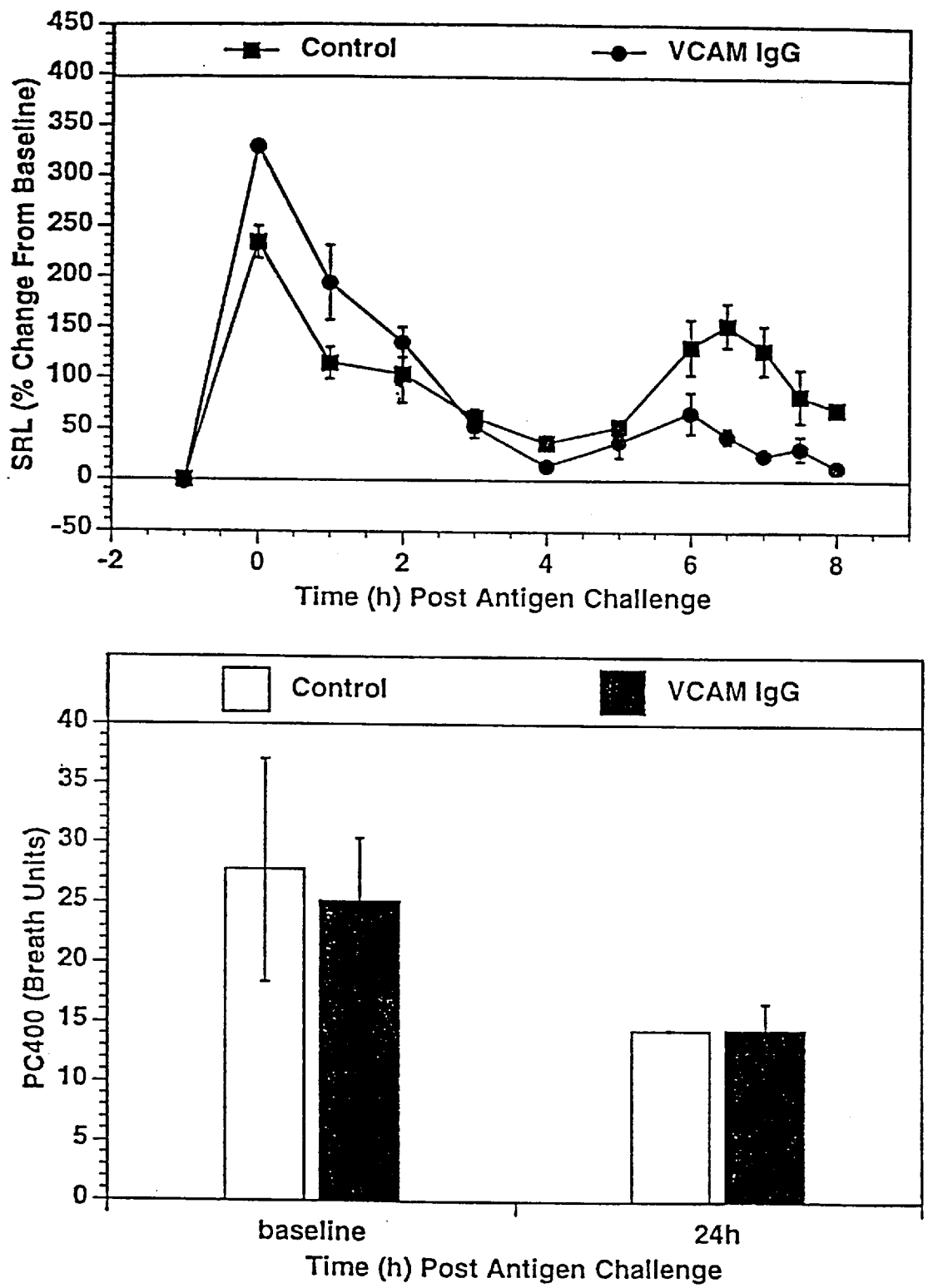
FIG. 8 is a graph depicting the effect of VCAM-Ig (30 mg, aerosol given 30 min before antigen challenge) on airway hyperresponsiveness in dual responder sheep. This dose resulted in significant but partial inhibition of LPR, but no effect on AHR.
Figure 9:
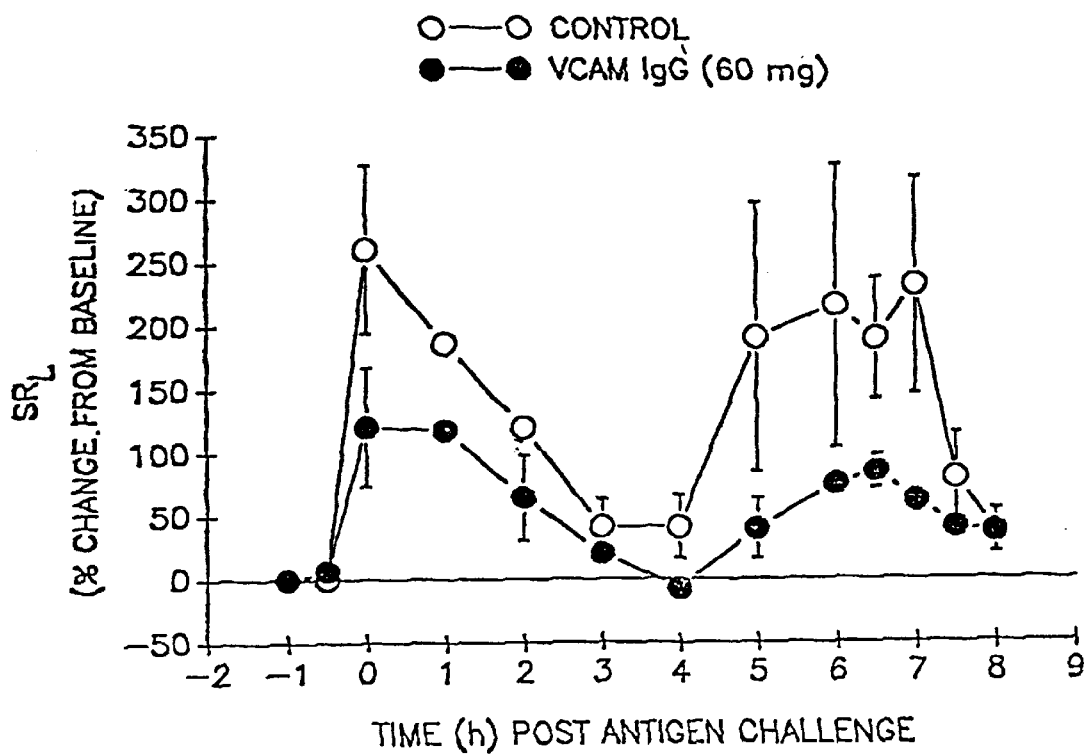
FIG. 9 is a graph depicting the effect of VCAM-Ig (60 mg, aerosol given 30 min before antigen challenge) on airway hyperresponsiveness in dual responder sheep. This dose resulted in significant but partial inhibition of LPR, and inhibition of AHR.
Figure 9:
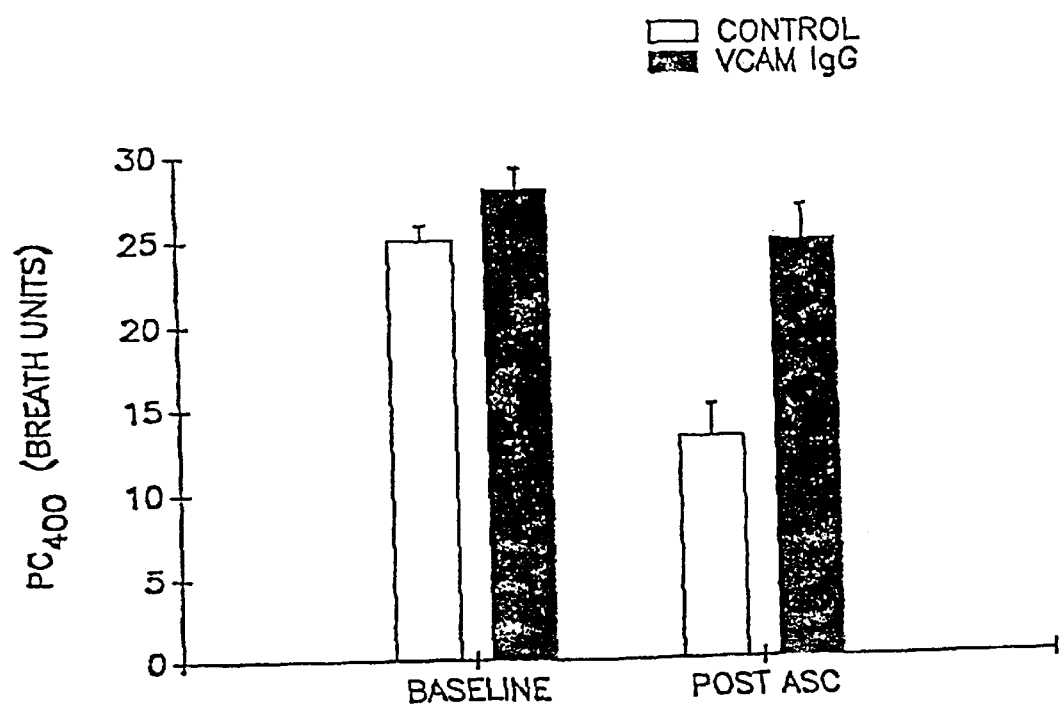
Figure 10:
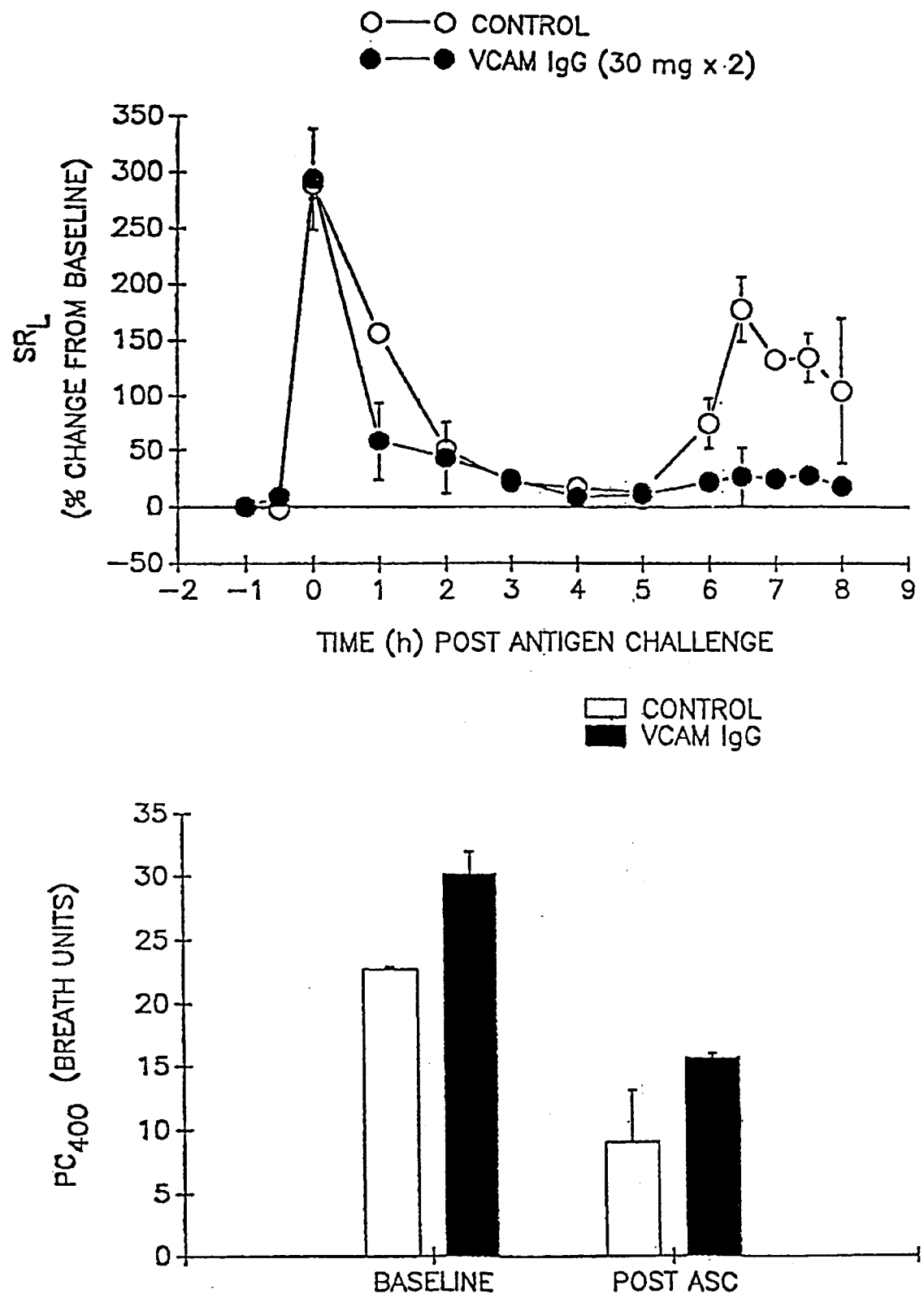
FIG. 10 is a graph depicting the effect of VCAM-Ig (30 mgs, aerosol given 30 min. before antigen challenge and 8 h. after challenge) on airway hyperresponsiveness in dual responder sheep. This dose resulted in complete inhibition of LPR, but no inhibition of AHR.
Figure 11:
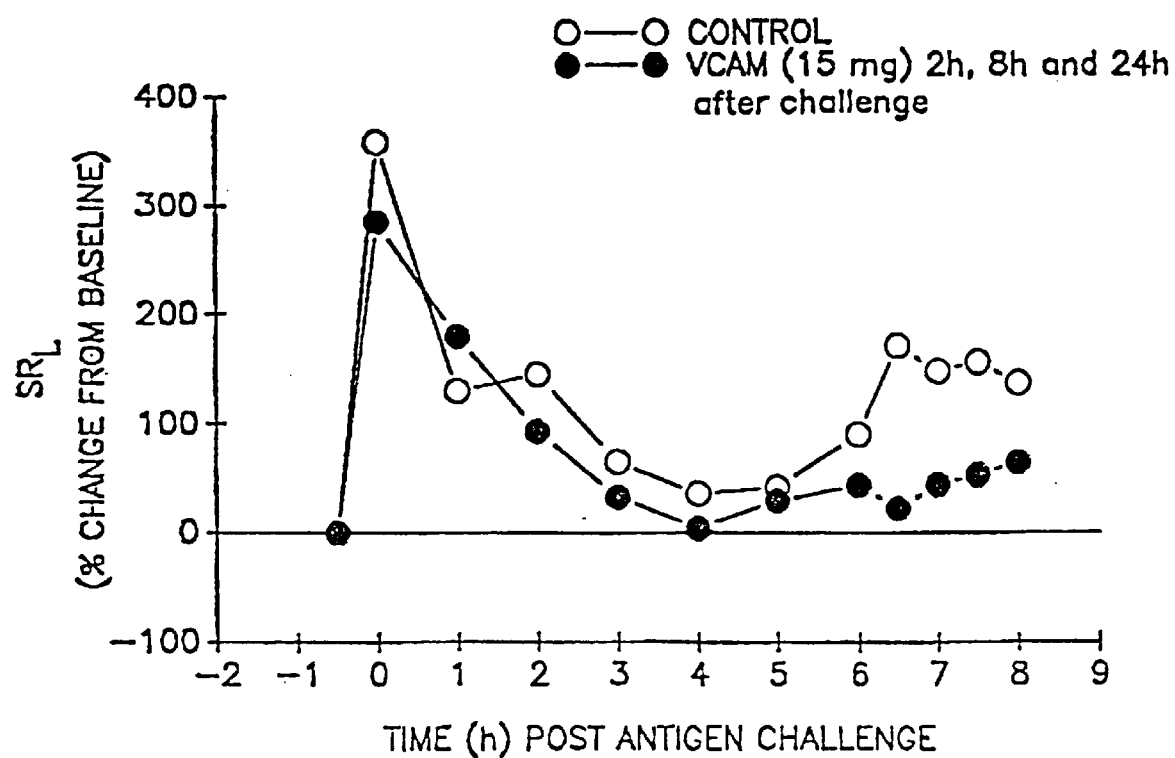
FIG. 11 is a graph depicting the effect of VCAM-Ig (15 mgs, aerosol given 2, 8 and 24 h. after antigen challenge) on airway hyperresponsiveness in dual responder sheep. This dose resulted in significant but partial inhibition of LPR, and inhibition of AHR.
Figure 11:
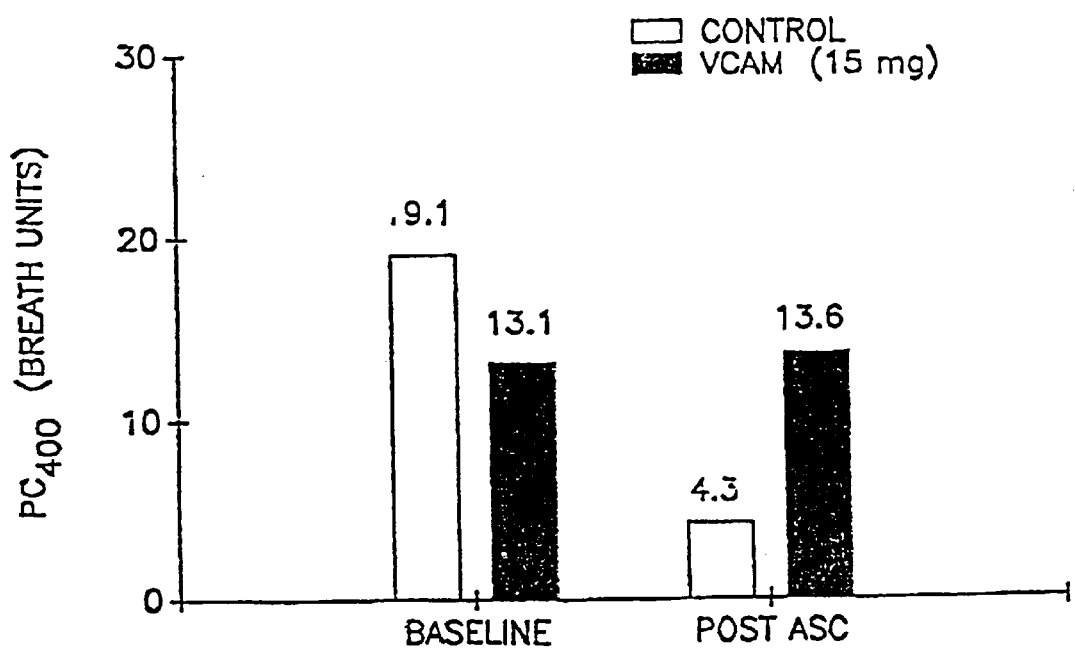
Figure 12:
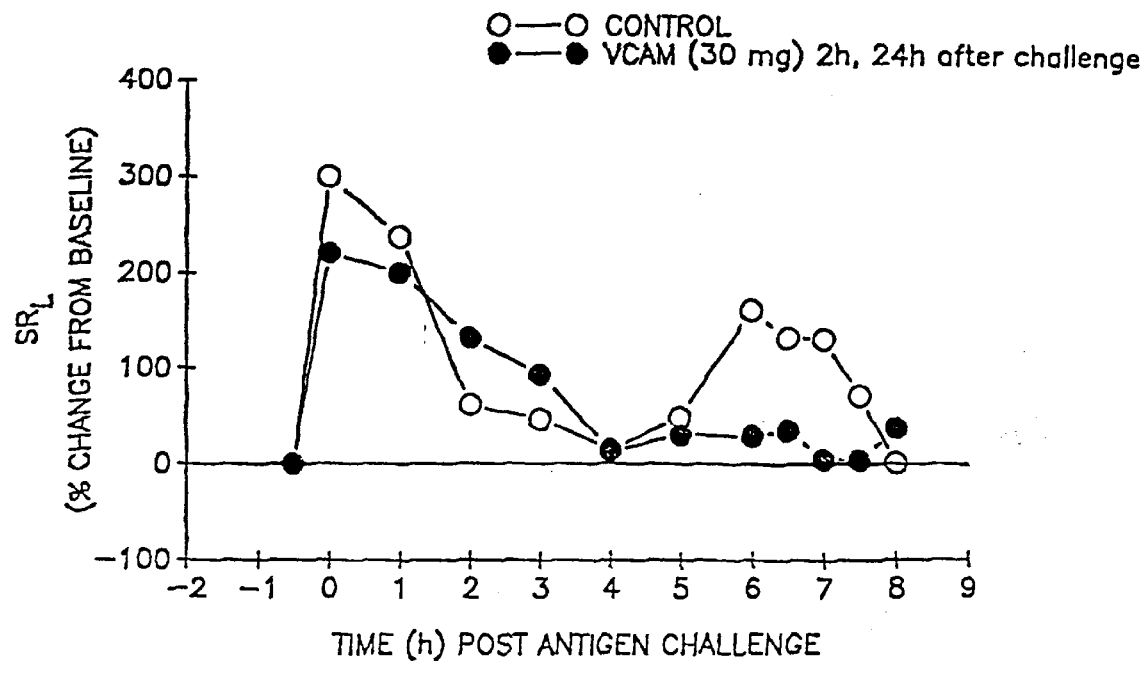
FIG. 12 is a graph depicting the effect of VCAM-Ig (30 mgs, aerosol given 2, and 24 h. after antigen challenge) on airway hyperresponsiveness in dual responder sheep. This optimal dose resulted in complete inhibition of both LPR and AHR.
Figure 12:
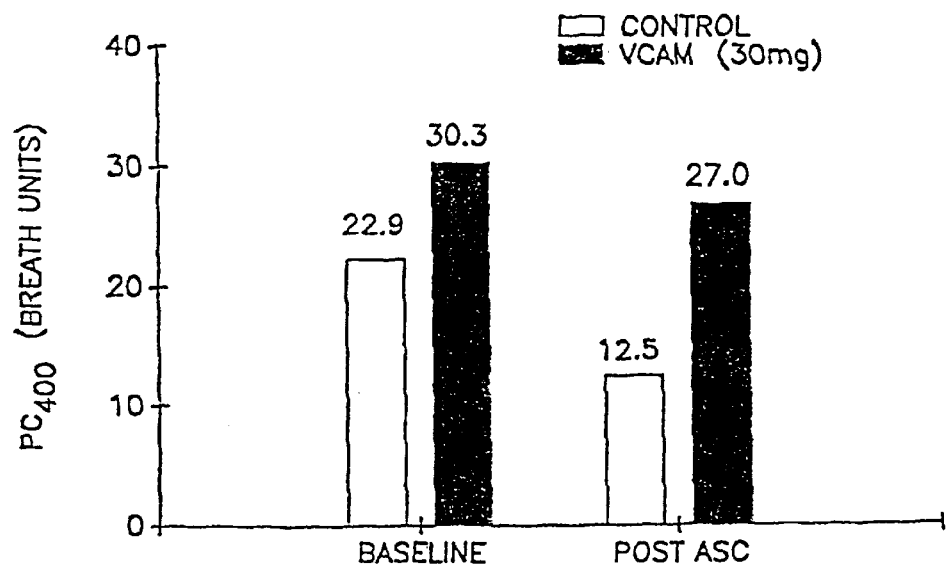

In order to optimize therapeutic efficacy, aerosolized VCAM-Ig was first administered at different dosing regimens. These experiments are summarized in FIGS. 8–12. In all the experiments, the control sheep received placebo. In the first experiment, two animals were given 30 mg VCAM-Ig (1 mg/kg) at 30 minutes prior to antigen challenge, which is the standard time used for other therapeutic agents (see Example 1 and 2). Under these conditions significant but partial inhibition of the late phase response (LPR) but no effect on airways hyper-responsiveness (AHR) was observed (FIG. 8). This result was not surprising as VCAM-Ig was found previously to be a little less potent than mAb HP1/2. In the second experiment, therefore, the dose of VCAM-Ig was increased to 60 mg. This dose resulted in the partial blockage of LPR as in the previous experiment, but now AHR was blocked too (FIG. 9). However, due to the serious problems which resulted from attempting to aerosolize such a large volume, in subsequent experiments dosages were administered at different time intervals. In the third experiment, 30 mg of VCAM-Ig were administered at 30 minutes prior to and 8 hours after antigen challenge. Here the LPR was blocked completely but no blockage of the AHR was observed (FIG. 10). With respect to the LPR this represented a single dose 30 minutes prior to antigen challenge (equivalent to experiment 1) because the second dose at 8 hours was given after the LPR was largely over. In the fourth experiment, 15 mg of VCAM-Ig were administered at 2, 8 and 24 hours. Here partial blockage of the LPR and blockage of the AHR was observed (FIG. 11). In the final experiment, 30 mg of VCAM-Ig were administered at 2 and 24 hours and resulted in complete blockage of both the LPR and AHR (FIG. 12). This optimal dosage was tested on four animals with the same result.

In summary, ten animals have all shown partial or complete inhibition of the LPR versus a placebo control, and complete inhibition of both the LPR and AHR can be achieved under optimal conditions (30 mg of VCAM-Ig administered at 2 and 24 hours after antigen challenge).

The foregoing examples are intended as an illustration of the method of the present invention and are not presented as a limitation of the invention as claimed hereinafter. From the foregoing disclosure, numerous modifications and additional embodiments of the invention will be apparent to those experienced in this art. For example, actual dosage used, the type of antibody or antibody fragment used, mode of administration, exact composition, time and manner of administration of the treatment, and many other features all may be varied without departing from the description above. All such modifications and additional embodiments are within the contemplation of this application and within the scope of the appended claims.

CITED PUBLICATIONS

[1] M. R. Sears, "Epidemiology of Asthma," in *Asthma as an Inflammatory Disease*, P. O'Byrne, ed. (Marcel Dekker, Inc.; New York 1990), pp. 15–48

[2] L. K. Altman, "Despite Gains in Treatment, Asthma Worsens," *New York Times*, The Doctor's World, Mar. 26, 1991

[3] C. Starr, "Treating Asthma: A Killer Gathers Strength," *Drug Topics*, cover story, issue of Apr. 8, 1991

[4] D. W. Cockcroft, "Atopy and Asthma," in *Asthma as an Inflammatorv Disease*, P. O'Byrne, ed. (Marcel Dekker, Inc.; New York 1990), pp. 103–125

[5] F. M. C. Cuss, "The Pharmnacology of Antiasthrna Medications," in *Asthma as an Inflammatory Disease*, P. O'Byrne, ed. (Marcel Dekker, Inc.; New York 1990), pp. 199–250

[6] P. M. O'Byme, "Airway Inflammation and Asthma," in *Asthma as an Inflammatory Disease*, P. O'Byrne, ed. (Marcel Dekker, Inc.; New York 1990), pp. 143–157

[7] J. C. Hogg, "Pathology of Asthma," in *Asthma as an Inflammatorv Disease*, P. O'Byrne, ed. (Marcel Dekker, Inc.; New York 1990), pp. 1–13

[8] W. M. Abraham et al., "Cellular Markers of Inflammation in the Airways of Allergic Sheep with and without Allergen-induced Late Responses," *Am. Rev. Respir. Dis.*, 138, 1565–1571 (1988)

[9] K. F. Chung, "Inflammatory Mediators in Asthma," in *Asthma as an Inflammatory Disease*, P. O'Byrne, ed. (Marcel Dekker, Inc.; New York 1990), pp. 159–183

[10] P. F. Weller et al., "Human eosinophil adherence to vascular endothelium mediated by binding to vascular cell adhesion molecule 1 and endothelial leukocyte adhesion molecule 1," Proc. Natl. Acad. Sci. USA, 88, 7430–7433 (1991)

[11] G. M. Walsh ct al., "Human Eosinophil, But Not Neutrophil, Adherence to IL-1-Stimulated Human Umbilical Vascular Endothelial Cells Is $\alpha_4\beta_1$ (Very Late Antigen-4) Dependent," *J. Immunol.*, 146, 3419–3423 (1991)

[12] B. S. Bochner et al., "Adhesion of Human Basophils, Eosinophils, and Neutrophils to Interleukin 1-activated Human Vascular Endothelial Cells: Contributions of Endothelial Cell Adhesion Molecules," *J. Exp. Med.*, 173, 1553–1556 (1991)

[13] A. Dobrina et al., "Mechanisms of Eosinophil Adherence to Cultured Vascular Endothelial Cells," *J. Clin. Invest.*, 88, 20–26 (1991)

[14] M. J. Elices et al., "VCAM-1 on Activated Endothelium Interacts with the Leukocyte Integrin VLA-4 at a Site Distinct from the VLA-4/Fibronectin Binding Site," *Cell*, 60, 577–584 (1990)

[15] Kohler and Milstein, "Continuous Cultures of Fused Cells Secreting Antibody of Predefined Specificity," *Nature*, 256, pp. 495–497 (1975)

[16] F. Sanchez-Madrid et al., "VLA-3: A novel polypeptide association within the VLA molecular complex: cell distribution and biochemical characterization", *Eur. J. Immunol.*, 16, 1343–1349 (1986)

[17] M. E. Hemler et al., "Characterization of the Cell Surface Heterodimer VLA-4 and Related Peptides," *J. Biol. Chem.*, 262(24), 11478–11485 (1987)

[18] L. Osborn et al., "Direct cloning of vascular cell adhesion molecule 1, a cytokine-induced endothelial protein that binds to lymphocytes," *Cell*, 59, 1203–1211 (1989)

[19] R. Pulido et al., "Functional Evidence for Three Distinct and Independently Inhibitable Adhesion Activities Mediated by the Human Integrin VLA-4," *J. Biol. Chem.*, 266(16), 10241–10245 (1991)

[20] W. M. Abraham, "Pharmacology of Allergen-Induced Early and Late Airway Responses and Antigen-Induced Airway Hyperresponsiveness in Allergic Sheep," *Pulmonary Pharmacology*, 2, pp. 33–40 (1989)

[21] P. T. Jones et al., "Replacing the Complementarity-Determining Regions in a Human Antibody with Those From a Mouse", *Nature*, 321, pp. 522–525 (1986)

[22] E. S. Ward et al., "Binding Activities of a Repertoire of Single Immunoglobulin Variable Domains Secreted From *Escherichia coli*", *Nature*, 341, pp. 544–546 (1989).

[23] U.S. Pat. No. 4,816,397, Boss et al., "Multichain Polypeptides Or Proteins And Processes For Their Production", Mar. 28, 1989.

[24] J. J. Devlin et al., "Random Peptide Libraries: A Source of Specific Protein Binding Molecules", *Science*, 249, pp. 40–406 (1990)

[25] J. K. Scott and G. P. Smith, "Searching for Peptide Ligands with an Epitope Library", *Science*, 249, pp. 386–390 (1990)

[26] U.S. Pat. No. 4,833,092, Geysen, "Method For Determining Mimotopes", May 23, 1989.

[27] R. H. Gundel et al., "Endothelial Leukocyte Adhesion Molecule-1 Mediates Antigen-induced Acute Airway Inflammation and Late-phase Airway Obstruction in Monkeys," *J. Clin. Invest.*, 88, 1407–1411 (1991)

[28] C. D. Wegner et al., "Intercellular Adhesion Molecule-1 (ICAM-1) in the Pathogenesis of Asthma," *Science*, 247, 456–459 (1990)

[29] Sambrook et al., "Polymerase chain reaction", *Molecular Cloning*, Vol. 3, 14.1–14.35 (1989)

[30] J. Barsoum, *DNA and Cell Biol.*, 9, 293–300 (1990)

The foregoing documents are incorporated herein by reference.

We claim:

1. A method for the treatment of asthma comprising administering to a mammal suffering from allergic asthma an antibody, or a fragment of said antibody, capable of binding to the B1 or B2 epitope of the $\alpha_4$ subunit of VLA-4, or a soluble VCAM-1 polypeptide that can bind to die VCAM-1-binding domain of VLA-4, or combinations of any of the foregoing, in an amount effective to provide inhibition of late phase response to an allergen to which the sufferer is hypersensitive or to provide decreased airway hypersensitivity in said mammal following allergen challenge.

2. The method of claim 1, wherein the antibody or antibody fragment is selected, respectively, from monoclonal antibody HP1/2, or Fab, Fab', F(ab')2 or F(v) fragments of HP1/2.

3. The method of claim 1, wherein the antibody is a monoclonal antibody, a chimeric antibody, or a recombinant antibody.

4. The method of claim 1, wherein the anti-VLA-4 antibody is HP1/2, or a fragment thereof capable of binding to VLA-4.

5. The method of claim 1, wherein the antibody, antibody fragment, or soluble VCAM-1 polypeptide that can bind to the VCAM-1-binding domain of VLA-4 is administered at a dosage so as to provide from 0.05 to 5.0 mg/kg of antibody, antibody fragment, or a soluble VCAM-1 polypeptide that can bind to the VCAM-1-binding domain of VLA-4, based on the weight of the asthma sufferer.

6. The method of claim 5, wherein the antibody, antibody fragment, or soluble VCAM-1 polypeptide that can bind to the VCAM-1-binding domain of VLA-4 is administered at a dosage so as to provide 1.0–2.0 mg/kg of antibody, antibody fragment, or a soluble VCAM-1polypeptide that can bind to the VCAM-1-binding domain of VLA-4, based on the weight of the asthma sufferer.

7. The method according to claim 1, wherein the antibody is administered in an amount effective to provide a plasma level of antibody in the mammal of at least 10 $\mu$g/ml over a period of 7 days.

8. A method for the treatment of asthma comprising administering to a mammal suffering from asthma a composition comprising a therapeutically effective amount of an anti-VLA-4 antibody, said antibody capable of recognizing the B1 or B2 epitope of the $\alpha$ chain of VLA-4.

9. The method of claim 8, wherein the anti-VLA-4 antibody composition is administered intravenously.

10. The method of claim 8, wherein the anti-VLA-4 antibody composition is administered in the form of an aerosol by inhalation.

11. The method of claim 8, wherein the anti-VLA-4 antibody is HP1/2, or a fragment thereof capable of binding to VLA-4.

12. The method of claim 8, wherein the composition is administered at a dosage so as to provide from 0.05 to 5.0 mg/kg of antibody, based on the weight of the asthma sufferer.

13. The method of claim 12, wherein the composition is administered at a dosage so as to provide 0.5 to 2.0 mg/kg of antibody, based on the weight of the asthma sufferer.

14. The method according to claim 8, wherein the composition is administered in an amount effective to provide a plasma level of antibody in the mammal of at least 10 $\mu$g/ml.

15. The method of claim 8, wherein the composition is administered prior to exposure to an allergen to which the asthma sufferer is hypersensitive.

16. The method of claim 8, wherein the mammal is a human.

17. The method of claim 8, wherein the composition is administered after exposure to an allergen to which said mammal is hypersensitive.

18. A method for the treatment of asthma comprising administering to a mammal suffering from asthma a soluble VCAM-1 polypeptide.

19. The method of claim 18, wherein said soluble VCAM-1 polypeptide is a VCAM-1 fusion protein.

20. The method of claim 19, wherein said fusion protein is a bifunctional VCAM-1/Ig fusion protein.

21. The method of claim 20, wherein said fusion protein is VCAM 2D-IgG.

22. A method for the treatment of asthma comprising administering to a mammal suffering from allergic asthma a monoclonal antibody, a recombinant antibody, a chimeric antibody, or a fragment of such antibodies, capable of binding to the B1 or B2 epitope of the $\alpha_4$ subunit of VLA-4, or combinations of any of the foregoing, in an amount effective to provide inhibition of late phase response to an allergen to which the sufferer is hypersensitive or to provide decreased airway hypersensitivity in said mammal following allergen challenge.

* * * * *